(12) United States Patent
Mueller et al.

(10) Patent No.: US 8,343,190 B1
(45) Date of Patent: Jan. 1, 2013

(54) SYSTEMS AND METHODS FOR SPINOUS PROCESS FIXATION

(75) Inventors: Richard Mueller, Carlsbad, CA (US); Benjamin Arnold, San Diego, CA (US); Eric Dasso, Encinitas, CA (US)

(73) Assignee: NuVasive, Inc., San Diego, CA (US)

( * ) Notice: Subject to any disclaimer, the term of this patent is extended or adjusted under 35 U.S.C. 154(b) by 657 days.

(21) Appl. No.: 12/412,354

(22) Filed: Mar. 26, 2009

Related U.S. Application Data

(60) Provisional application No. 61/039,761, filed on Mar. 26, 2008, provisional application No. 61/123,783, filed on Apr. 11, 2008.

(51) Int. Cl.
*A61B 17/58* (2006.01)

(52) U.S. Cl. .......................................... 606/248; 606/71

(58) Field of Classification Search .......... 606/246–260, 606/70, 71, 297; 623/17.11; 403/53, 54, 403/58, 59, 68, 73, 84
See application file for complete search history.

(56) References Cited

U.S. PATENT DOCUMENTS

| | | | |
|---|---|---|---|
| 267,269 A | 11/1882 | Smith et al. |
| 2,677,369 A | 5/1954 | Knowles |
| 3,025,853 A | 3/1962 | Mason |
| 3,242,922 A | 3/1966 | Thomas |
| 3,426,364 A | 2/1969 | Lumb |
| 3,648,691 A | 3/1972 | Lumb et al. |
| 3,805,219 A | 4/1974 | Bright |
| 4,143,883 A | 3/1979 | Paynter |
| 4,448,191 A | 5/1984 | Rodnyansky et al. |
| 4,554,914 A | 11/1985 | Kapp et al. |
| 4,570,618 A | 2/1986 | Wu |
| 4,604,995 A | 8/1986 | Stephens et al. |
| 4,643,178 A | 2/1987 | Nastari et al. |
| 4,655,462 A | 4/1987 | Balsells |
| 4,773,402 A | 9/1988 | Asher et al. |
| 4,913,134 A | 4/1990 | Luque |
| 5,011,484 A | 4/1991 | Breard |
| 5,084,049 A | 1/1992 | Asher et al. |
| 5,092,866 A | 3/1992 | Breard et al. |
| 5,167,662 A | 12/1992 | Hayes et al. |
| 5,180,393 A | 1/1993 | Commarmond |
| 5,261,914 A | 11/1993 | Warren |
| 5,304,178 A | 4/1994 | Stahurski |
| 5,352,225 A | 10/1994 | Yuan et al. |
| 5,470,333 A | 11/1995 | Ray |
| 5,496,318 A | 3/1996 | Howland et al. |
| 5,531,747 A | 7/1996 | Ray |

(Continued)

FOREIGN PATENT DOCUMENTS

DE 3114872 10/1982

(Continued)

*Primary Examiner* — Alvin Stewart
*Assistant Examiner* — Tara Carter
(74) *Attorney, Agent, or Firm* — NuVasive, Inc.; Jonathan Spangler; Jennifer Russell

(57) ABSTRACT

A spinal fixation device including two plates and a coupling element for coupling the plates in a fixed manner about adjacent spinous processes of the spine. Each plate is preferably equipped with integral spikes on the inwardly facing surfaces for pressing into the spinal processes and thereby augmenting the purchase between the plates and the spinous processes. Each plate contains a central aperture through which the coupling element passes in order to couple the plates together.

15 Claims, 31 Drawing Sheets

U.S. PATENT DOCUMENTS

| | | |
|---|---|---|
| 5,609,634 A | 3/1997 | Voydeville |
| 5,645,599 A | 7/1997 | Samani |
| 5,722,976 A | 3/1998 | Brown |
| 5,836,948 A | 11/1998 | Zucherman et al. |
| 6,048,342 A | 4/2000 | Zucherman et al. |
| 6,312,431 B1 | 11/2001 | Asfora |
| 6,364,883 B1 | 4/2002 | Santilli |
| 6,582,433 B2 | 6/2003 | Yun |
| 6,626,944 B1 | 9/2003 | Taylor |
| 6,641,585 B2 | 11/2003 | Sato et al. |
| 6,652,527 B2 | 11/2003 | Zucherman et al. |
| 6,652,534 B2 | 11/2003 | Zucherman et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,761,720 B1 | 7/2004 | Senegas |
| 6,796,983 B1 | 9/2004 | Zucherman et al. |
| 7,048,736 B2 | 5/2006 | Robinson et al. |
| 7,201,775 B2 | 4/2007 | Gorensek et al. |
| 7,252,673 B2 | 8/2007 | Lim |
| 7,306,628 B2 | 12/2007 | Zucherman et al. |
| 7,361,179 B2 | 4/2008 | Rousseau et al. |
| 7,520,888 B2 | 4/2009 | Trieu |
| 7,588,592 B2 | 9/2009 | Winslow et al. |
| 7,727,233 B2 | 6/2010 | Blackwell et al. |
| 7,758,274 B2 * | 7/2010 | Paul .......................... 403/109.3 |
| 7,776,069 B2 | 8/2010 | Taylor |
| 7,828,847 B2 | 11/2010 | Abdou |
| 7,837,688 B2 | 11/2010 | Boyer, II et al. |
| 7,842,074 B2 | 11/2010 | Abdou |
| 2001/0021850 A1 | 9/2001 | Zucherman et al. |
| 2003/0040746 A1 | 2/2003 | Mitchell et al. |
| 2003/0065330 A1 * | 4/2003 | Zucherman et al. ............ 606/61 |
| 2003/0094812 A1 | 5/2003 | Balsells |
| 2003/0216736 A1 | 11/2003 | Robinson et al. |
| 2003/0236472 A1 | 12/2003 | Van Hoeck et al. |
| 2004/0260291 A1 | 12/2004 | Jensen |
| 2005/0033434 A1 | 2/2005 | Berry |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2006/0036256 A1 | 2/2006 | Carl et al. |
| 2006/0036258 A1 | 2/2006 | Zucherman et al. |
| 2006/0064095 A1 | 3/2006 | Senn et al. |
| 2006/0106381 A1 | 5/2006 | Ferree et al. |
| 2006/0106397 A1 | 5/2006 | Lins |
| 2006/0136060 A1 | 6/2006 | Taylor |
| 2006/0235532 A1 | 10/2006 | Meunier et al. |
| 2006/0241601 A1 | 10/2006 | Trautwein et al. |
| 2006/0247633 A1 * | 11/2006 | Winslow et al. ................ 606/61 |
| 2006/0247640 A1 * | 11/2006 | Blackwell et al. ............... 606/71 |
| 2006/0293662 A1 | 12/2006 | Boyer, II et al. |
| 2007/0093823 A1 | 4/2007 | Booth et al. |
| 2007/0093825 A1 | 4/2007 | Ferree et al. |
| 2007/0093828 A1 | 4/2007 | Abdou |
| 2007/0100340 A1 | 5/2007 | Lange et al. |
| 2007/0173832 A1 | 7/2007 | Tebbe et al. |
| 2007/0225724 A1 | 9/2007 | Edmond |
| 2007/0233074 A1 | 10/2007 | Anderson et al. |
| 2007/0233077 A1 | 10/2007 | Khalili |
| 2007/0233088 A1 | 10/2007 | Edmond |
| 2007/0233096 A1 | 10/2007 | Garcia-Bengochea |
| 2007/0233129 A1 | 10/2007 | Bertagnoli et al. |
| 2007/0270812 A1 | 11/2007 | Peckham |
| 2007/0270824 A1 | 11/2007 | Lim et al. |
| 2007/0270827 A1 | 11/2007 | Lim et al. |
| 2007/0270874 A1 | 11/2007 | Anderson |
| 2007/0276370 A1 | 11/2007 | Altarac et al. |
| 2007/0299445 A1 | 12/2007 | Shadduck et al. |
| 2008/0027438 A1 | 1/2008 | Abdou |
| 2008/0033552 A1 | 2/2008 | Lee et al. |
| 2008/0039837 A1 | 2/2008 | Gambale |
| 2008/0051896 A1 | 2/2008 | Suddaby |
| 2008/0114401 A1 | 5/2008 | Liu et al. |
| 2008/0114455 A1 | 5/2008 | Lange et al. |
| 2008/0140125 A1 | 6/2008 | Mitchell et al. |
| 2008/0161818 A1 | 7/2008 | Kloss et al. |
| 2008/0167655 A1 | 7/2008 | Wang et al. |
| 2008/0177271 A1 | 7/2008 | Yeh |
| 2008/0177298 A1 | 7/2008 | Zucherman et al. |
| 2008/0177391 A1 | 7/2008 | Mitchell et al. |
| 2008/0234735 A1 | 9/2008 | Joshi |
| 2008/0269904 A1 | 10/2008 | Voorhies |
| 2008/0281359 A1 | 11/2008 | Abdou |
| 2008/0294199 A1 | 11/2008 | Kohm et al. |
| 2008/0300686 A1 | 12/2008 | Khoo |
| 2008/0312741 A1 | 12/2008 | Lee et al. |
| 2009/0054931 A1 | 2/2009 | Metz-Stavenhagen |
| 2009/0062915 A1 | 3/2009 | Kohm et al. |
| 2009/0062918 A1 | 3/2009 | Wang et al. |
| 2009/0082808 A1 | 3/2009 | Butler et al. |
| 2009/0105773 A1 | 4/2009 | Lange et al. |
| 2009/0198277 A1 | 8/2009 | Gordon et al. |
| 2009/0204151 A1 | 8/2009 | Bracken |
| 2009/0326581 A1 | 12/2009 | Galley et al. |
| 2010/0069965 A1 | 3/2010 | Abdou |
| 2010/0087869 A1 | 4/2010 | Abdou |
| 2010/0211102 A1 | 8/2010 | Belliard et al. |
| 2010/0318128 A1 | 12/2010 | Abdou |
| 2011/0004248 A1 | 1/2011 | Abdou |

FOREIGN PATENT DOCUMENTS

| | | |
|---|---|---|
| EP | 1872731 | 1/2008 |
| FR | 1037262 | 9/1953 |
| FR | 2703239 | 10/1994 |
| FR | 2806614 | 9/2001 |
| FR | 2902639 | 12/2007 |
| FR | 2930718 | 11/2009 |
| GB | 780652 | 8/1957 |
| WO | WO 93/14721 | 8/1993 |
| WO | WO 94/20048 | 9/1994 |
| WO | WO 03/007829 | 1/2003 |
| WO | WO 03/024298 | 3/2003 |
| WO | WO 2004/039283 | 5/2004 |
| WO | WO 2006/086241 A2 | 8/2006 |
| WO | WO 2006/110578 | 10/2006 |
| WO | WO 2007/038475 | 4/2007 |
| WO | WO 2007/087535 A2 | 8/2007 |
| WO | WO 2007/089975 | 8/2007 |
| WO | WO 2007/106573 | 9/2007 |
| WO | WO 2008/067452 | 6/2008 |
| WO | WO 2008/106140 | 9/2008 |
| WO | WO 2009/135208 | 11/2009 |
| WO | WO 2009/152126 | 12/2009 |

* cited by examiner

SYSTEMS AND METHODS FOR SPINOUS PROCESS FIXATION

CROSS REFERENCE TO RELATED APPLICATIONS

The present application is a nonprovisional patent application claiming the benefit of priority under 35 U.S.C. §119(e) from U.S. Provisional Application No. 61/039,761, filed on Mar. 26, 2008, and U.S. Provisional Application No. 61/123,783, filed on Apr. 11, 2008, the entire contents of which are hereby expressly incorporated by reference into this disclosure as if set forth fully herein.

BACKGROUND OF THE INVENTION

I. Field of the Invention

The present invention relates generally to spinal surgery, and more particularly to devices for fusing adjacent spinous processes to stabilize the vertebral segment associated with the particular spinous processes.

II. Discussion of the Prior Art

The human spinal column is made up of two basic components, vertebrae (bone) and intervertebral discs (gel-like cushions that absorb pressure and prevent vertebrae from rubbing together). A number of vertebrae and intervertebral discs stack together to form a column that provides support and structure for the body while still allowing a large degree of motion and flexibility. The spinal column also serves to protect the spinal cord (a bundle of nerves linking the brain to the rest of the body) that runs through an opening formed in the center of the column. A pair of nerve roots exit the spinal column at each level through spaces formed between the vertebrae. Various traumatic events and degenerative conditions may result in undesirable motion or changes in disc height, both of which may cause chronic pain for the affected individual. The pain is generally caused when changes in disc height and improper motion allow adjacent vertebrae to impinge upon exiting nerve roots. The degree and treatment of pain varies by individual but in many instances the pain can be disabling and uncontrollable by non-invasive means, leaving surgery as the only viable option. Generally in such a case, two or more vertebrae are fused together, employing various instrumentation and methods to correct disc height and prevent improper movement of the vertebrae while fusion occurs, thereby eliminating or at least reducing the pain of the affected individual.

While there are a variety of systems and methods for effecting spinal fixation while fusion occurs, one of the more common methods involves securing pedicle screws into the pedicles of the two or more adjacent vertebrae to be fixed. The challenge in this method is securing the pedicle screws without breaching, cracking, or otherwise compromising the pedicle wall, which may occur if the screw is not properly aligned with the pedicle axis. If the pedicle (or more specifically, the cortex of the medial wall, lateral wall, superior wall and/or inferior wall) is breached, cracked, or otherwise compromised, the patient may experience pain or neurological deficit due to unwanted contact between the pedicle screw and delicate neural structures, such as the spinal cord or exiting nerve roots. This may necessitate revision surgery, which is disadvantageously painful for the patient and costly, both in terms of recovery time and hospitalization.

The present invention is directed to overcome one or more shortcomings encountered with current fixation devices and systems.

SUMMARY OF THE INVENTION

The present invention relates to a spinal fixation device designed to be attached to adjacent spinous processes of the spine for immobilizing the adjacent spinous processes to promote fusion therebetween. The spinal fixation device may be used alone (that is, without any supplemental fusion devices, such as interbody fusion implants) or with supplemental fixation devices. In either event, the spinal fixation device allows fusion to occur between the adjacent spinous processes by maintaining them in an immobilized, locked relationship such that a boney bridge can form therebetween. The formation of the fusion bridge between the adjacent spinous processes may be augmented or facilitated by placing fusion-enhancing compounds between the spinous processes, including but not limited to allograft bone, autograft bone, bone morphogenic protein (BMP), calcium hydroxyapatite, demineralized bone matrix, collagen bone graft matrix (e.g. Formagraft®), and stem cell material (e.g. Osteocel®) and/or any number of suitable biomaterials.

According to one embodiment of the present invention, the spinal fixation device includes two plates and a coupling element for coupling the plates in a fixed manner about adjacent spinous processes of the spine. Each plate is preferably equipped with integral spikes on the inwardly facing surfaces for pressing into the spinal processes and thereby augmenting the purchase between the spinous processes and the plates. Each plate contains a central aperture through which the coupling element passes in order to couple the plates together.

The coupling element may be any number of devices capable of coupling the first plate to the second plate. In one embodiment, the coupling element may be an elongated bolt member having external ridges (as opposed to threads) to engage corresponding features in the aperture of one plate to prevent any backward motion once received through the aperture. This embodiment is advantageous in that the plates can be easily locked together and tightened by simply pushing the coupling element through one plate (with the head received within a corresponding region or recess of the first plate) and into the next (with the ridges locking at each point as the ridged section is advanced through the aperture of the second plate, the head may or may not be fully contained within the first plate). In either embodiment, the head may be constructed like a screw head with an internally disposed recess for receiving a driving element (e.g. hexalobe drive, Phillips screw driver, hex driver, etc. . . . ) or may be constructed without such an internally disposed recess and may instead be driven by an exteriorly placed driving element (e.g. wrench).

The apertures may be provided in any number of different manners to help facilitate coupling the fixation element to the plates. For example, the aperture of one plate may be equipped with any number of suitable features, such as inwardly facing teeth or ridges that engage with the ridges of the coupling element. Moreover, the aperture may include a recess therein configured to house a locking element in the form of a canted coil ring member. The coiled ring member is configured to allow uni-directional movement while in a compressed state and bi-directional movement of the coupling element while in a relaxed state.

Any number of suitable instruments may be provided to help facilitate the surgery, including but not limited to instruments for compressing and/or distracting the adjacent spinous processes prior to securing the plates (and thus immobilizing the spinous processes), as well as instruments to facilitate coupling the plates together such as drivers for tightening the coupling element to the plates or instruments for compressing the plates together. In one embodiment, the driving or compressing instrument may be equipped with a torque limiting mechanism that produces an audible (e.g. "click") and/or and a tactile alert that lets the surgeon know he or she has applied optimal torque to the fixation element to fix the plates together.

DESCRIPTION OF THE PREFERRED EMBODIMENT

Figure 1:
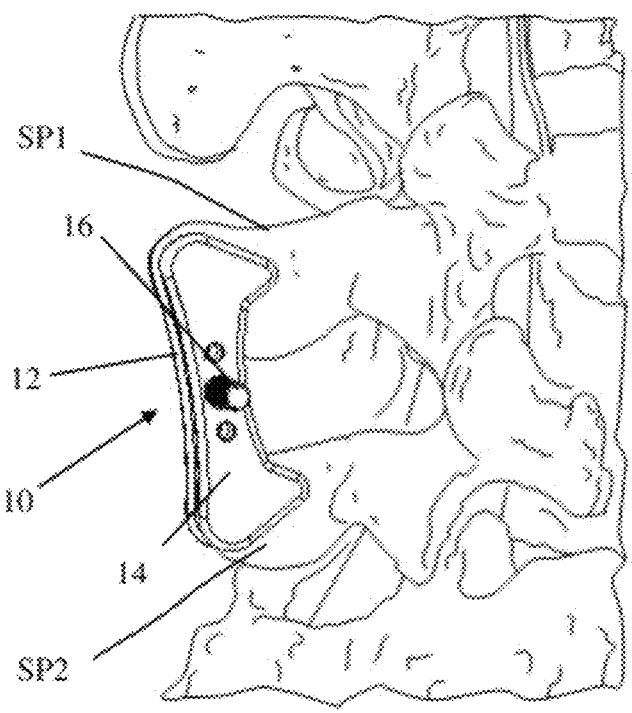
FIG. 1 is a postero-lateral view of a portion of the spine with one example of a spinous process fixation system according to one embodiment of the present invention implanted on adjacent spinous processes.
Figure 2:
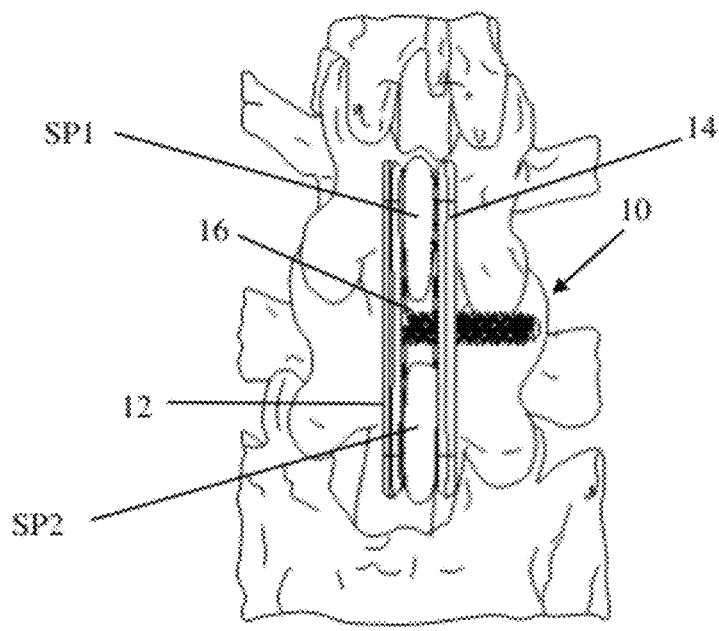
FIG. 2 is a posterior view of the spinous process fixation system implanted on adjacent spinous processes as shown in FIG. 1.
Figure 3:
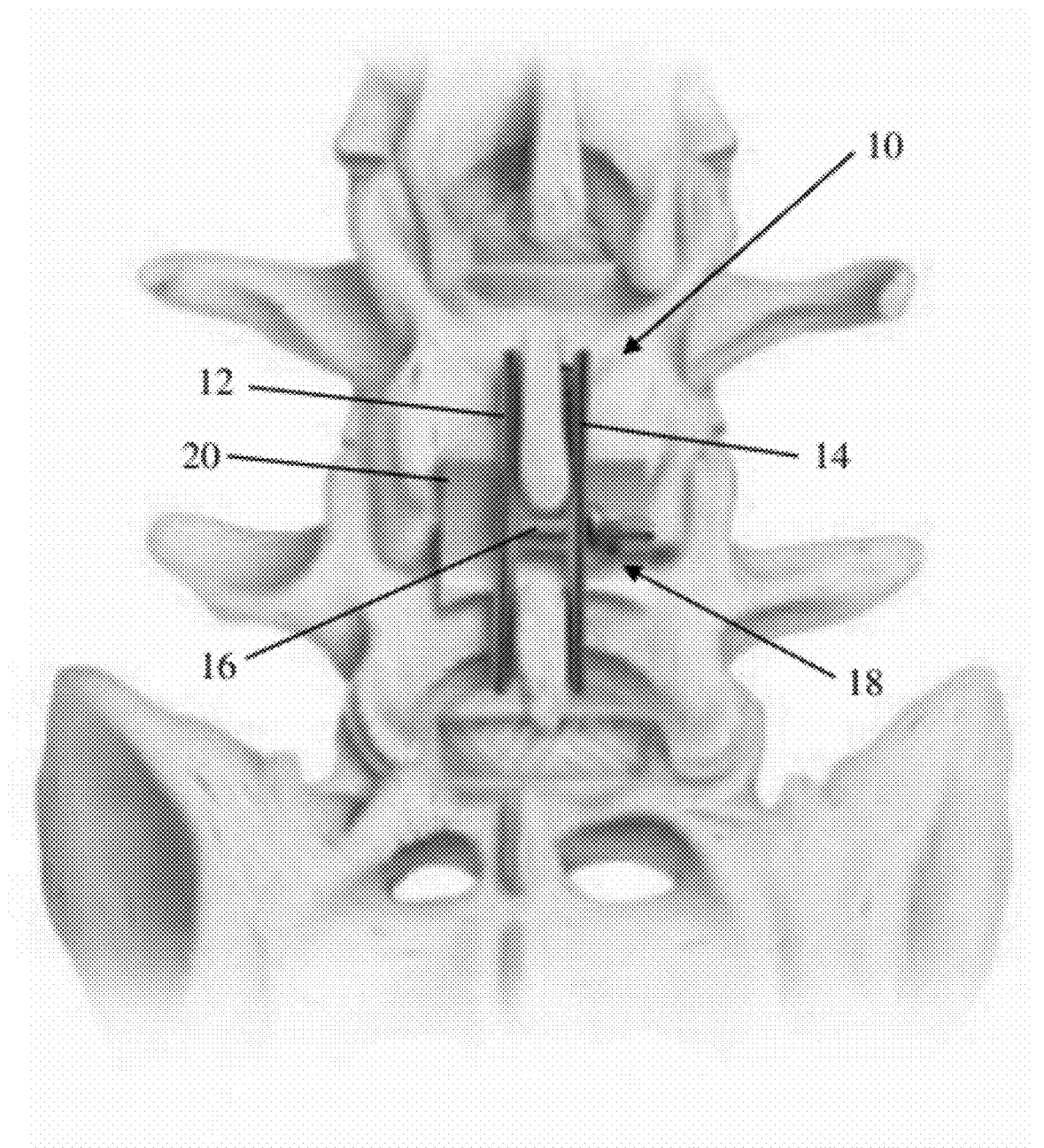
FIG. 3 is a posterior view of the spinous process fixation system of FIG. 1 implanted on adjacent spinous processes used in conjunction with a fusion implant.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinous process plate system for spinal fusion disclosed herein boasts a variety of inventive features and components that warrant patent protection, both individually and in combination FIGS. 1-3 illustrate an example of a spinous process fixation system 10 according to one embodiment of the present invention attached to adjacent spinous processes SP1, SP2 of a spine. The spinous process fixation system 10 includes a first plate 12, a second plate 14, a coupling element 16, and a locking assembly 18 (FIG. 3). The spinous process fixation system 10 is designed to be attached to adjacent spinous processes SP1, SP2 of the spine for immobilizing the adjacent spinous processes SP1, SP2 to promote fusion therebetween. The system 10 may be used alone (that is, without any supplemental fusion devices, such as interbody fusion implants) as shown in FIGS. 1-2. Alternatively, the system 10 may be used with supplemental devices, for example such as a fusion implant 20 (FIG. 3). In any event, the system 10 allows fusion to occur between the adjacent spinous processes SP1, SP2 by maintaining them in an immobilized, locked relationship such that a boney bridge can form therebetween. The formation of the fusion bridge between the adjacent spinous processes SP1, SP2 may be augmented or facilitated by placing fusion-enhancing compounds between the spinous processes (such as, e.g. between the plates 12, 14 or within the fusion implant 20 or other supplemental device), including but not limited to allograft bone, autograft bone, bone morphogenic protein (BMP), calcium hydroxyapatite, demineralized bone matrix, collagen bone graft matrix (e.g. Formagraft®), and stem cell material (e.g. Osteocel®) and/or any number of suitable biomaterials.

Figure 4:
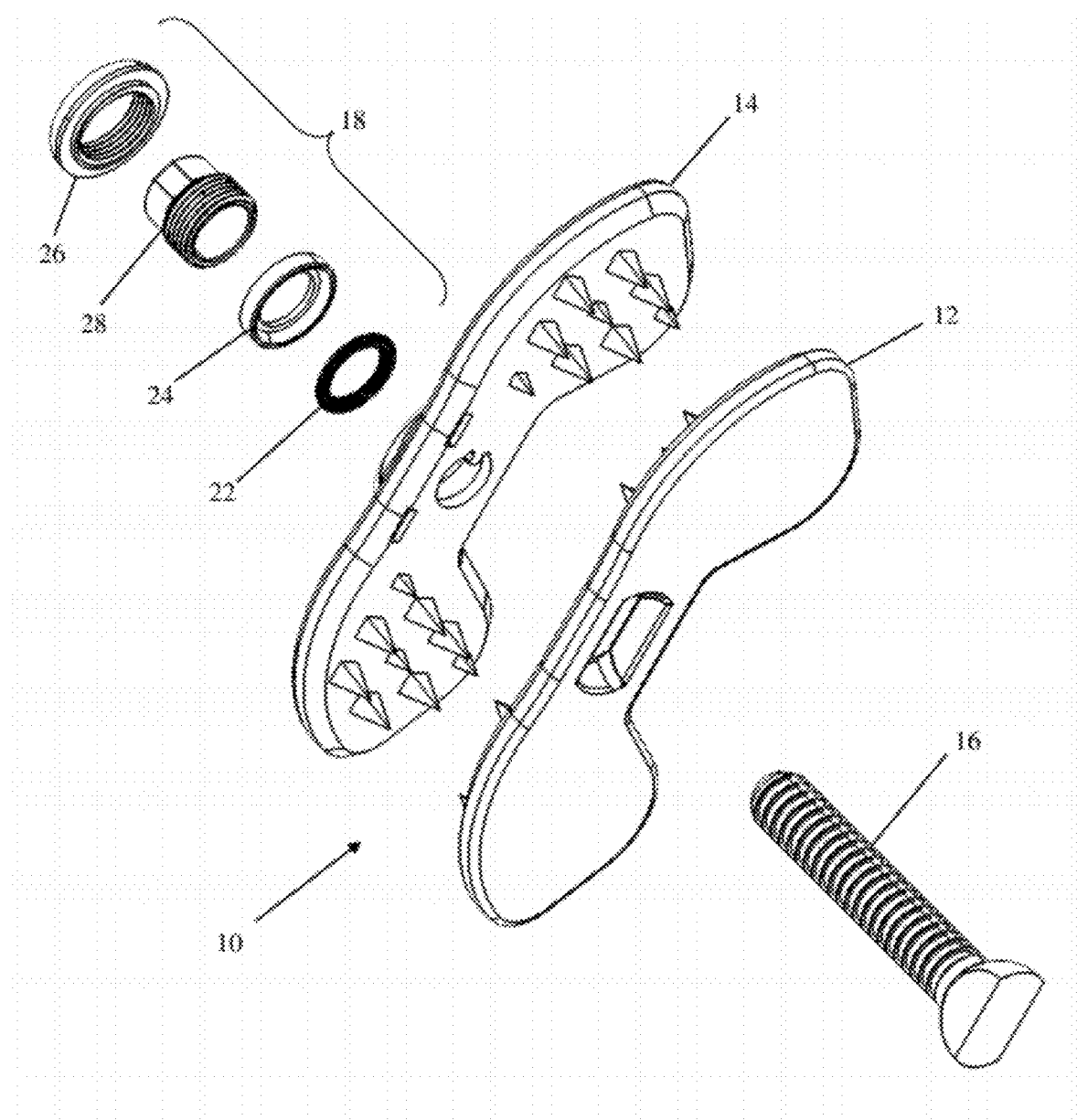
FIG. 4 is an exploded view of the spinous process fixation system of FIG. 1.

The specifics of the spinous process fixation system 10 will now be described with reference to FIGS. 4-38. FIG. 4 illustrates the spinous process fixation system 10 in exploded view. The spinous process fixation system 10 includes a first plate 12, a second plate 14, a coupling element 16, and a locking assembly 18. The locking assembly 18 includes a locking element 22, compression member 24, locking cap 26, and lock nut 28. As will be explained in further detail below, the locking assembly 18 is configured to be assembled with the second plate 14 and provides secure coupling of the coupling member, which in turn maintains the first and second plates 12, 14 in a desired orientation relative to one another.

Figure 5:
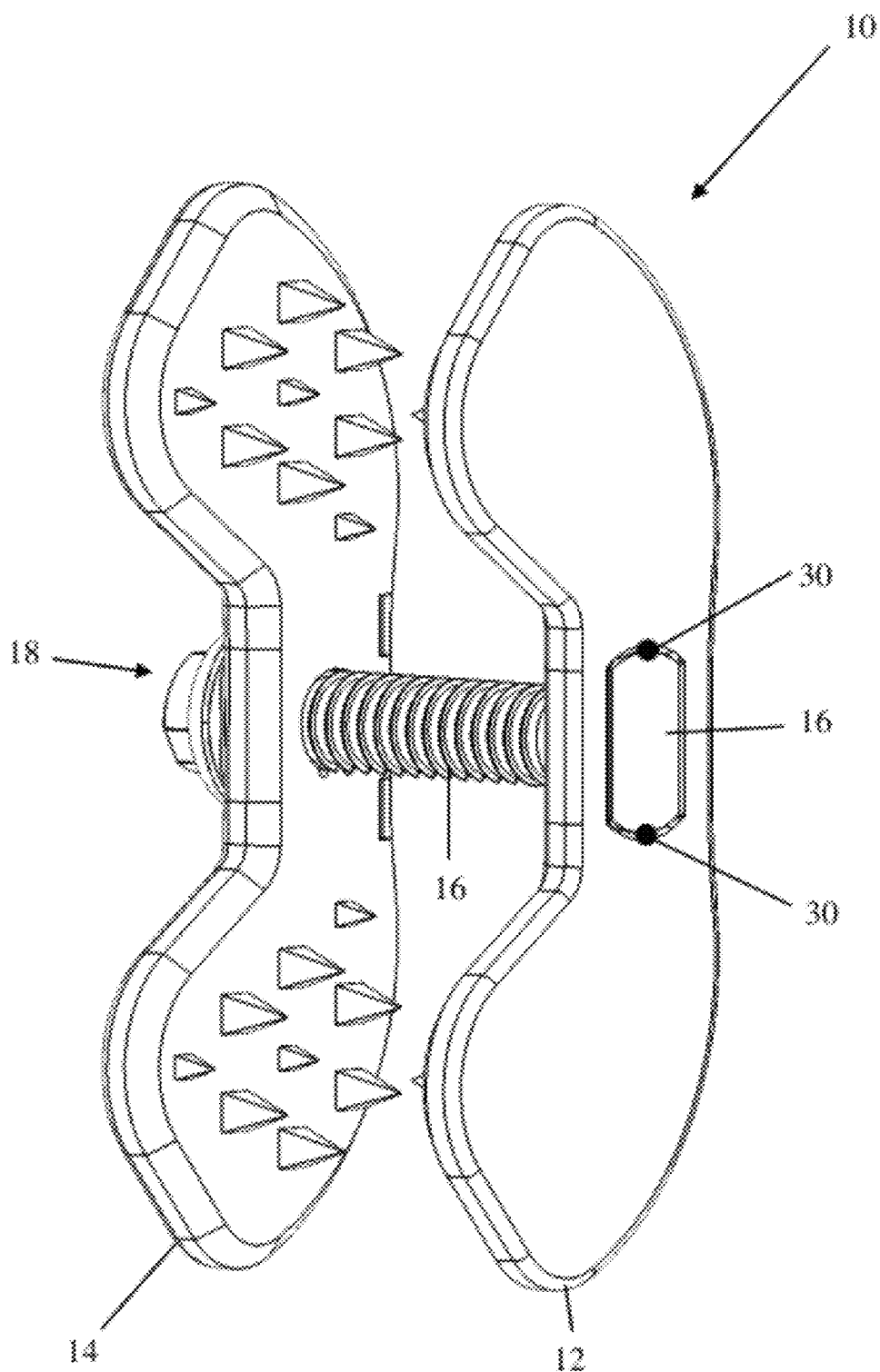
FIGS. 5-6 are perspective views of the assembled spinous process fixation system of FIG. 4.
Figure 6:
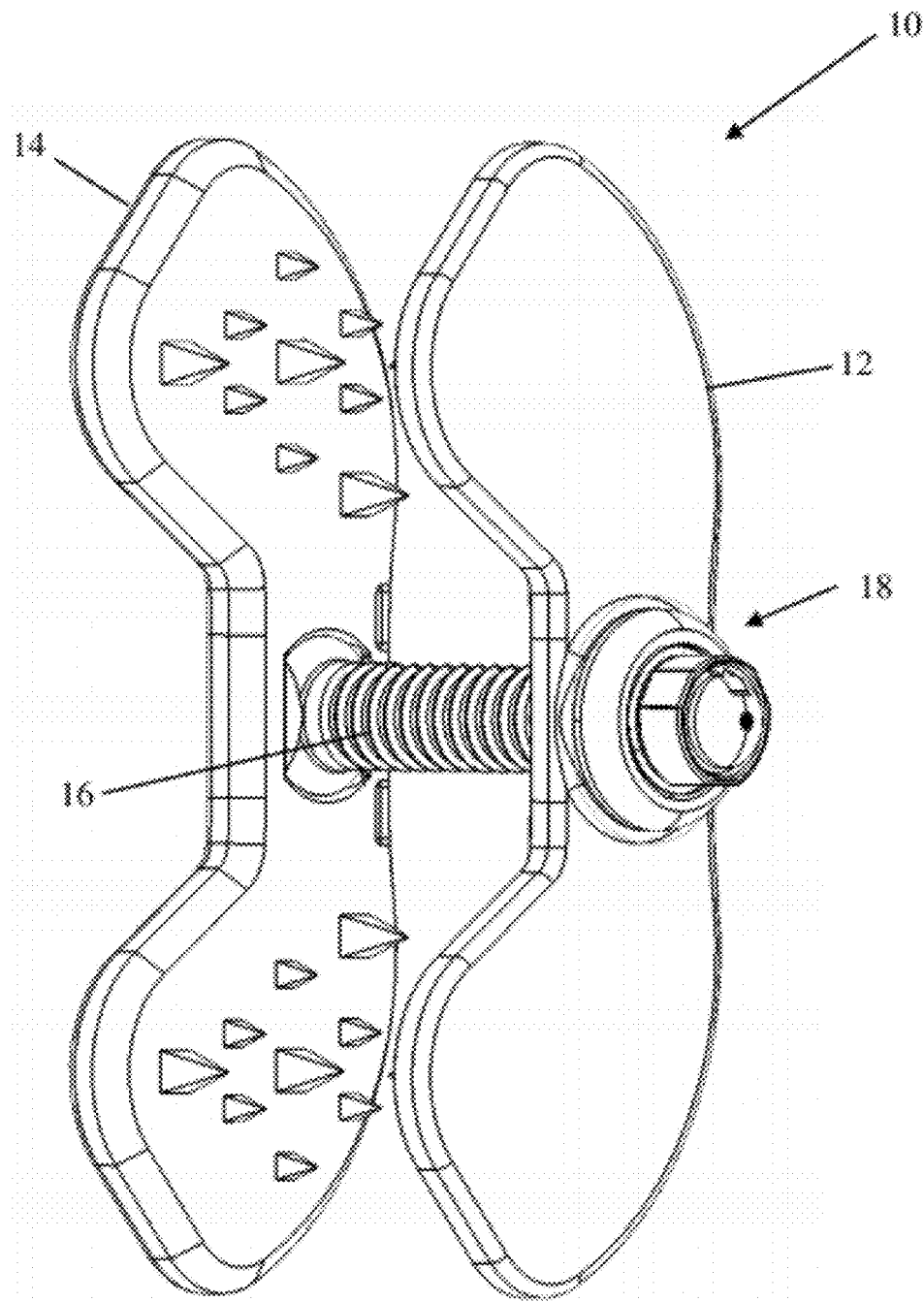

FIGS. 5 and 6 illustrate the spinous process fixation system 10 in an assembled but pre-compressed state. By way of example only, the spinous process fixation system 10 may be provided to the user in such an orientation, with the first and second plates 12, 14 separated by a predetermined distance (e.g. sufficient to allow for a disposition of the spinous processes SP1, SP2 between the plates 12, 14). In the optional preassembled position, the locking assembly 18 is coupled to the second plate 14, and the first and second plates 12, 14 are coupled by coupling element 16. Optionally, coupling element 16 may be temporarily fixed to the first plate 12 by at least one spot welding 30. Spot welding 30 further helps keep the first and second plates 12, 14 in a desired orientation relative to one another prior to implantation of the spinous process fixation system 10 within the spinal column.

Figure 7:
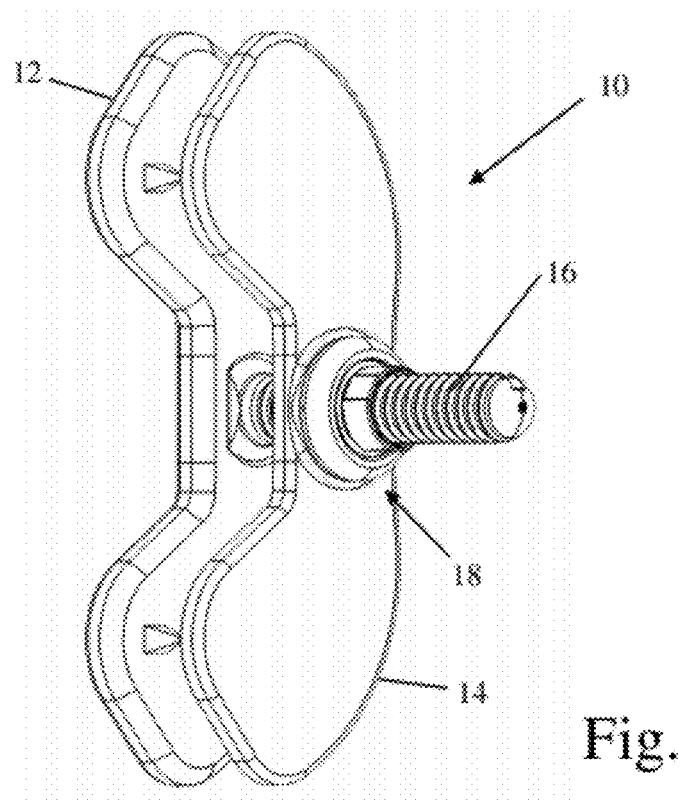
FIGS. 7-8 are perspective and plan views, respectively, of the spinous process fixation system of FIG. 4 in a second, compressed position.
Figure 8:
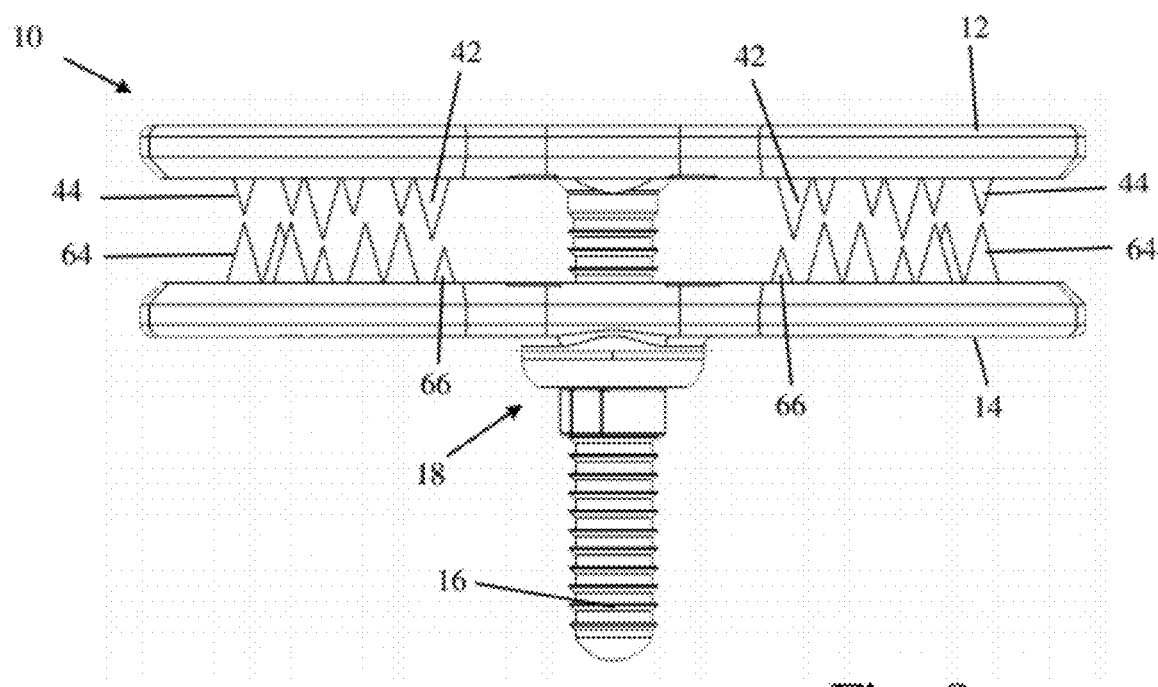

FIGS. 7 and 8 illustrate the spinous process fixation system 10 in a compressed state. The plates 12, 14 may be compressed to a separation of any desirable distance, however, the distance will be controlled by the width of at least one of the spinous processes SP1, SP2 that are to be fixed using the spinous process fixation system 10. Upon compression of the spinous process fixation system 10, a distal portion of the shaft 122 of the coupling element 16 protrudes beyond the profile of the plating system 10. This distal portion may be left intact, or in the alternative may be removed using an appropriate cutting device (not shown). FIG. 8 also shows the relative positioning of major and minor spike elements 42, 44, respectively, of first plate 12 and major and minor spike elements 64, 66 respectively, of second plate 14 upon compression of the spinous process fixation system 10. The specifics of these features are discussed in further detail below.

Figure 9:
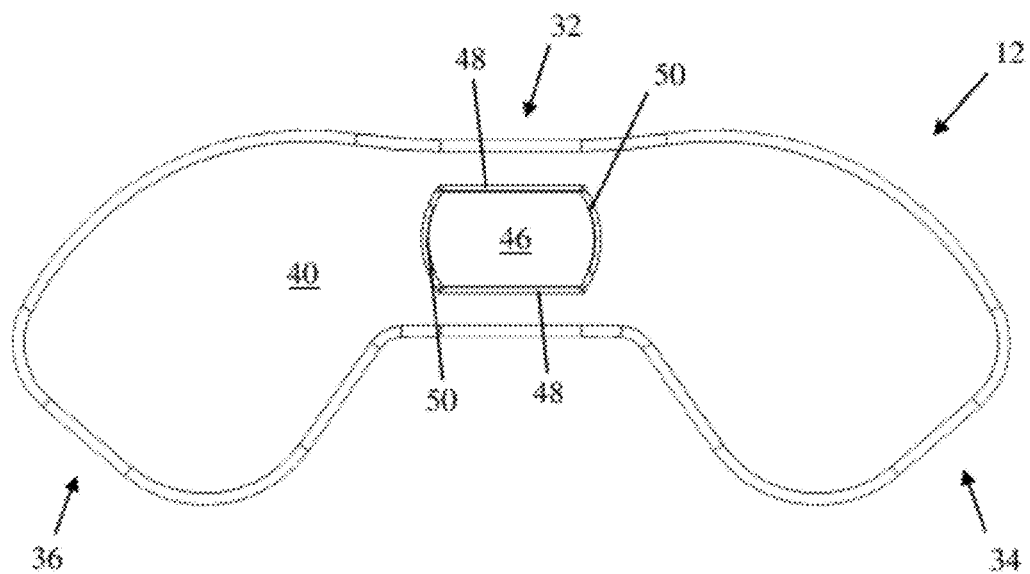
FIGS. 9-10 are top and bottom plan views, respectively, of a first plate forming part of the spinous process fixation system of FIG. 4.
Figure 10:
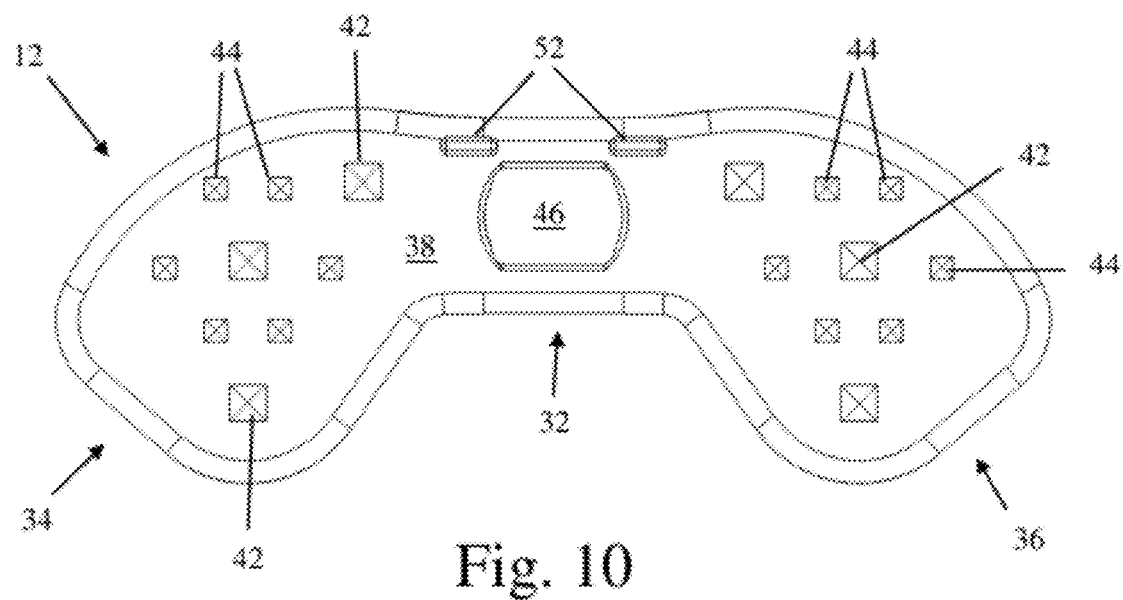

The first plate 12 will now be described with specific reference to FIGS. 9-13. The first plate 12 includes a central body portion 32 extending between a pair of end portions 34, 36. The first plate 12 further includes a first surface 38 dimensioned to face medially, or toward the second plate 14 when assembled and a second surface 40 dimensioned to face laterally, or away from the second plate 14 when assembled. The central body portion 32 may have a generally curved perimeter and (as best viewed in FIGS. 9-10) has a width less than the width of the end portions 34, 36. The increased width of the end portions 34, 36 is designed to present a relatively large footprint on the adjacent spinous processes SP1, SP2, which helps in establishing a robust engagement therewith while avoiding protrusion beyond the spinous processes SP1, SP2. Although generally "hook" shaped in the embodiment shown, one of ordinary skill in the art will appreciate that the end portions 34, 36 may be provided in any number of suitable shapes including but not limited to generally rectangular, generally triangular, and generally rounded. As shown in FIG. 10, this engagement may be augmented through the use of a plurality of major and minor spike elements 42, 44, respectively, disposed on the first surface 38 of the first plate 12, at the end portions 34, 36. These spike elements 42, 44 are designed to become embedded in the lateral surface of the spinous processes SP1, SP2 when the spinous process fixation system 10 is compressed in place as shown in FIGS. 1-3. As described in further detail below, the spike elements 42, 44 are provided in an arrangement complimentary to that of the spike elements 64, 66 of the second plate 14 to increase purchase within the spinous process bone.

Figure 11:
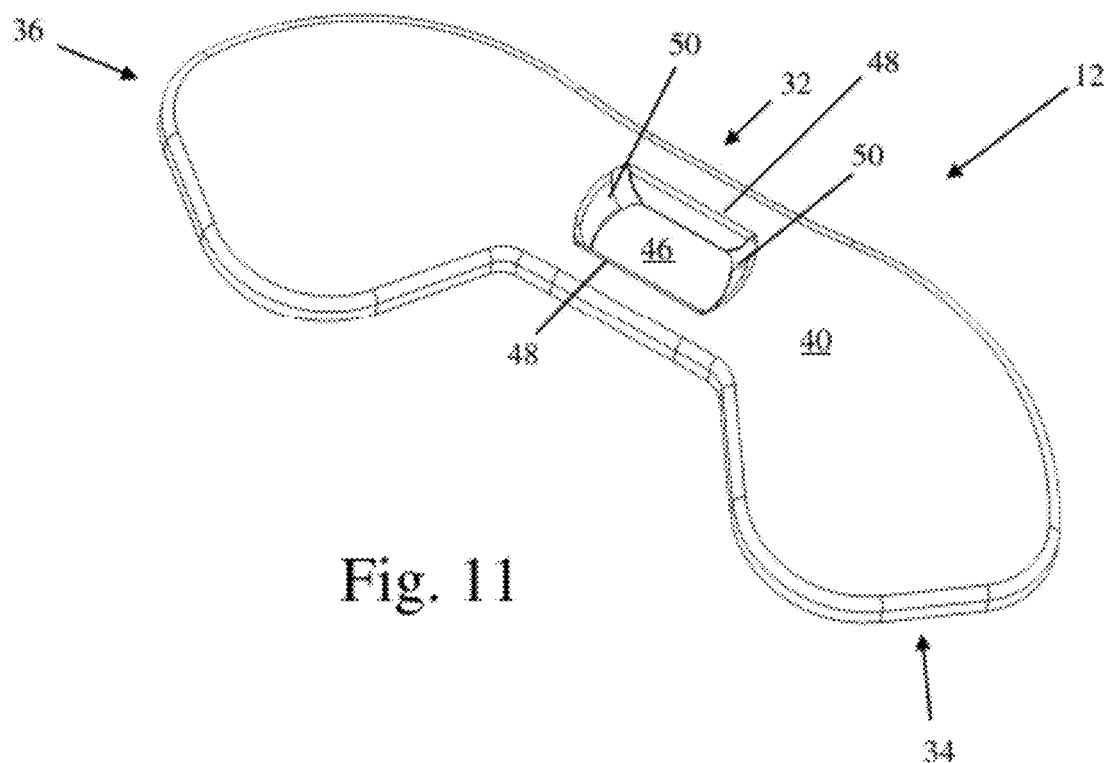
FIGS. 11-12 are top and bottom perspective views, respectively, of the first plate of FIG. 9.
Figure 12:
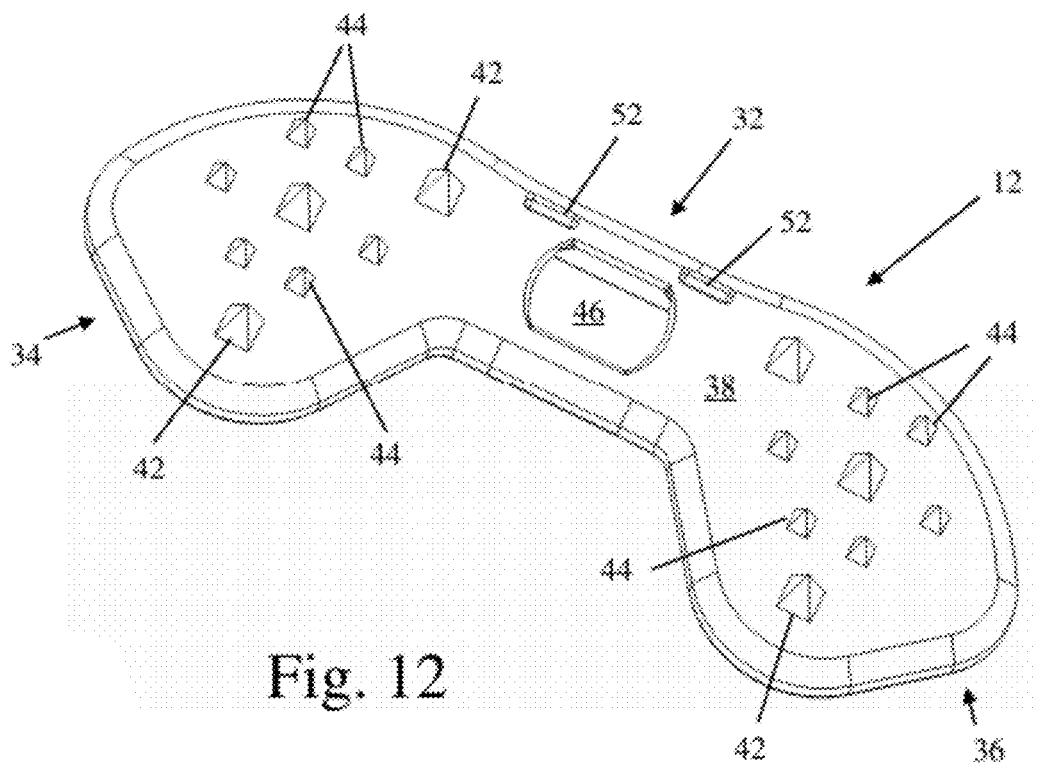
Figure 13:
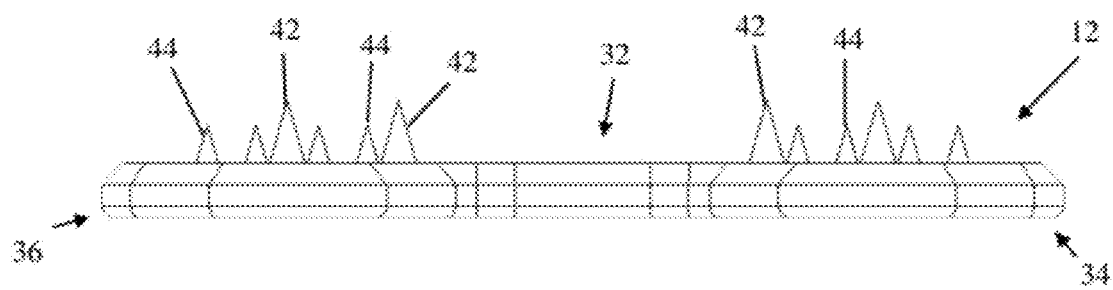
FIG. 13 is a side plan view of the first plate of FIG. 9.
Figure 14:
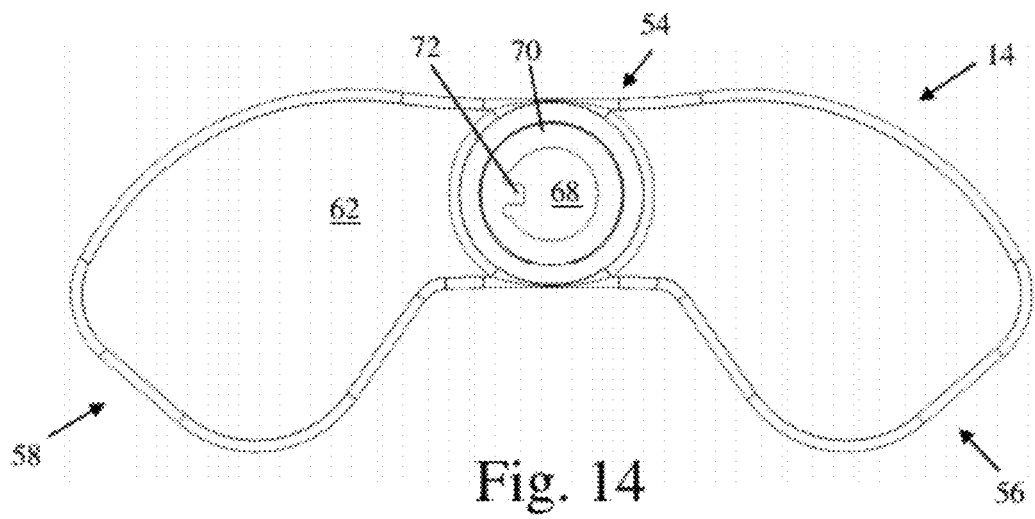
FIGS. 14-15 are top and bottom plan views, respectively, of a second plate forming part of the spinous process fixation system of FIG. 4.
Figure 35:
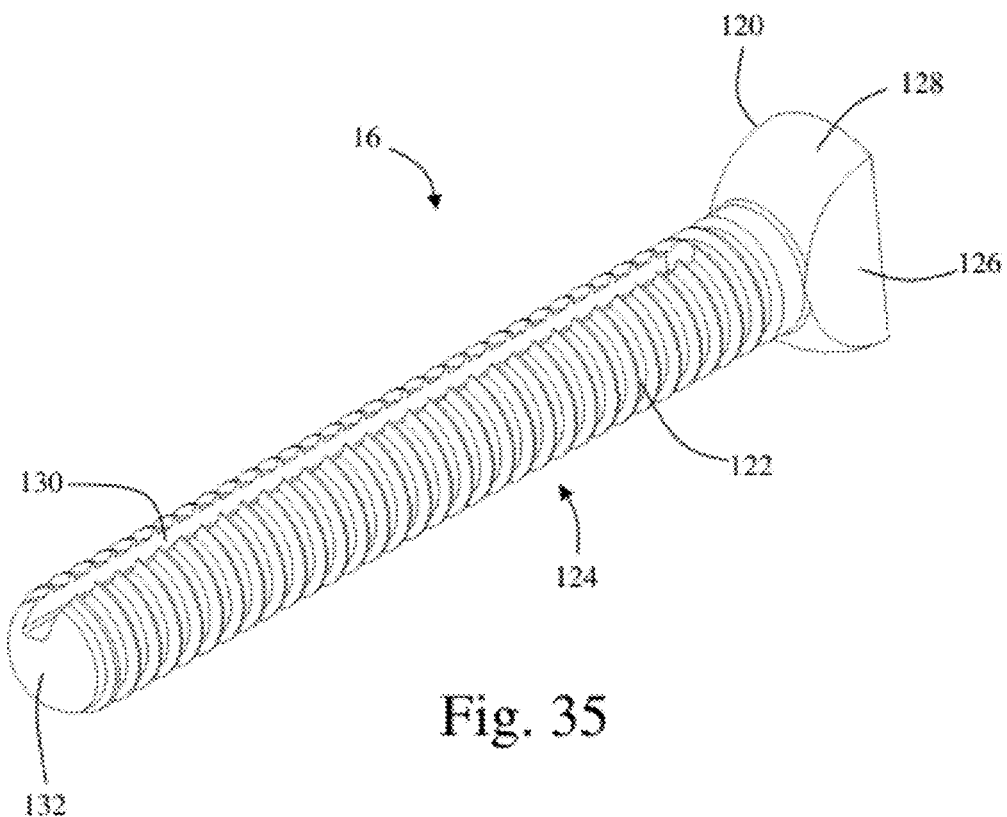
FIGS. 35-36 are perspective and plan views, respectively, of one example of a coupling element forming part of the spinous process fixation system of FIG. 4.
Figures 36, 37:
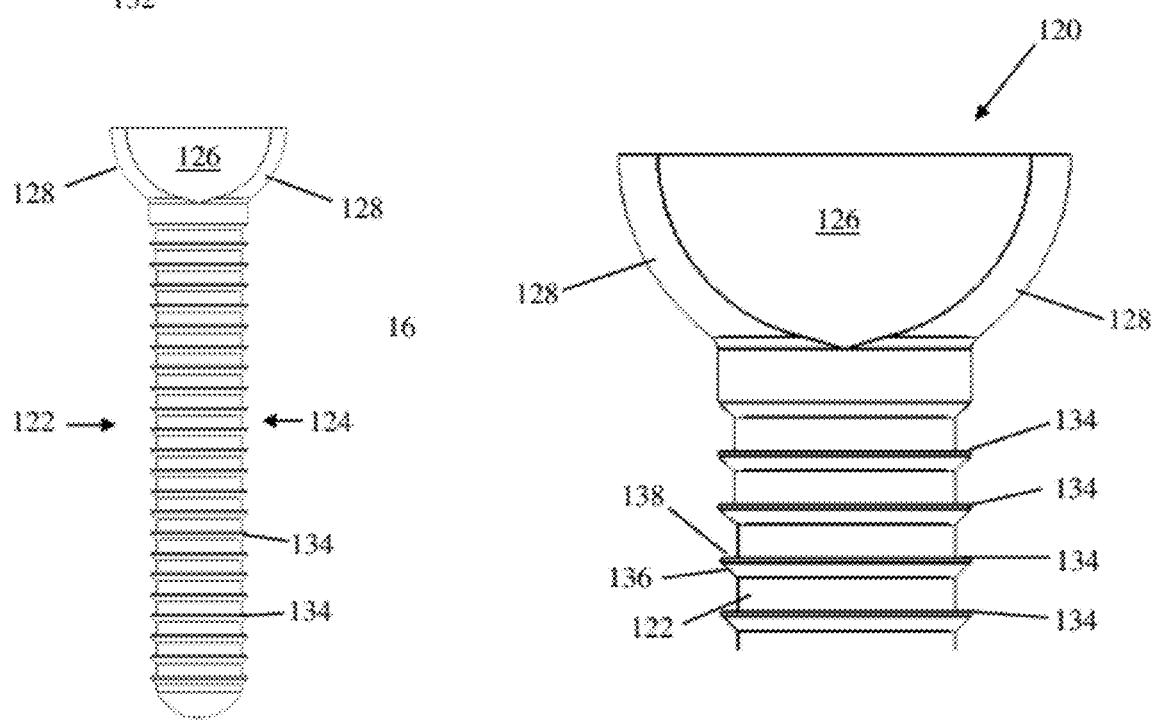
FIG. 37 is a plan view of the head region of the coupling element of FIG. 35.

The first plate 12 includes a central aperture 46 dimensioned to receive a proximal end 132 of the coupling element 16. More specifically, as best shown in FIGS. 9 and 11, the central aperture 46 is a "truncated spherical" recess having straight sides 48 and semi-spherical end regions 50. The straight sides 48 and semi-spherical end regions 50 are dimensioned to receive the generally straight sides 126 and semi-spherical end regions 128 of the head 120 of the coupling element 16 (FIGS. 35-37). The first plate 12 also, according to one embodiment, includes elongated recesses 52 formed within first surface 38 and positioned on either side of the central aperture 46. Each recess 52 is dimensioned to receive an extension element of an insertion tool, for example such as inserter 400 shown and described below in relation to FIGS. 52-56. The insertion tool may be used to hold and manipulate the first plate 12 as needed to properly position it on the desired spinous processes SP1, SP2.

The first plate 12 may be constructed from any of a variety to suitable materials without departing from the scope of the invention, including but not limited to titanium, polymeric materials (e.g. plastics such as poly-ether-ether-ketone) carbon fiber, and/or any other biologically acceptable material. The first plate 12 may also be provided with any number of suitable dimensions without departing from the scope of the invention. For example, according to one embodiment, the width of the central body portion 32 may range from 5 mm to 20 mm, the width of the end portions 34, 36 may range from 7.5 mm to 25 mm, the length of the central body portion 32 may range from 1 mm to 65 mm, the length of the end portions 34, 36 may range from 7.5 mm to 25 mm, and the thickness of the first plate 12 may range from 1.5 mm to 15 mm. It will be appreciated, however, that these dimensions are provided as examples of those that may be employed with the spinous process fixation system 10 of the present invention and any number of suitable modifications may be made depending upon a variety of factors without departing from the scope of the invention.

Figure 15:
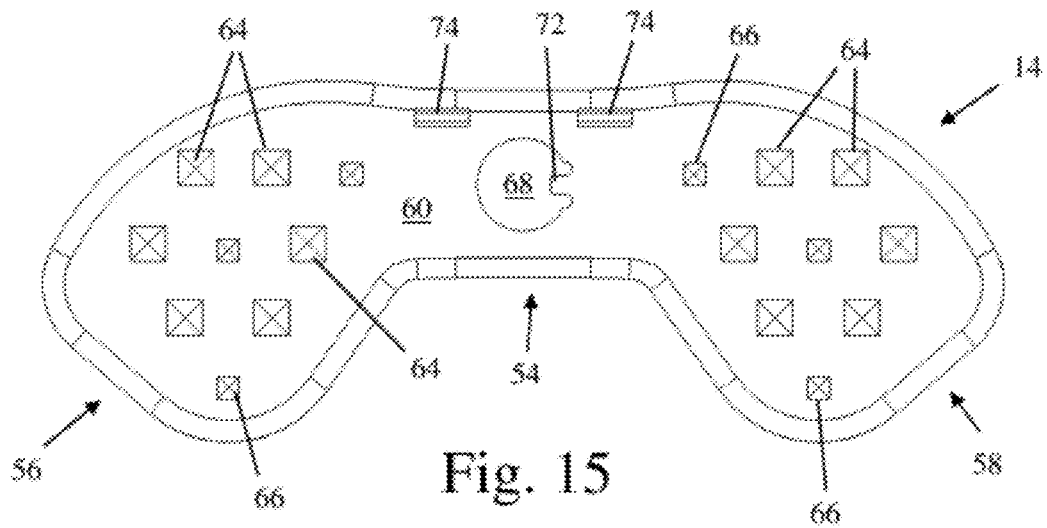
Figure 16:
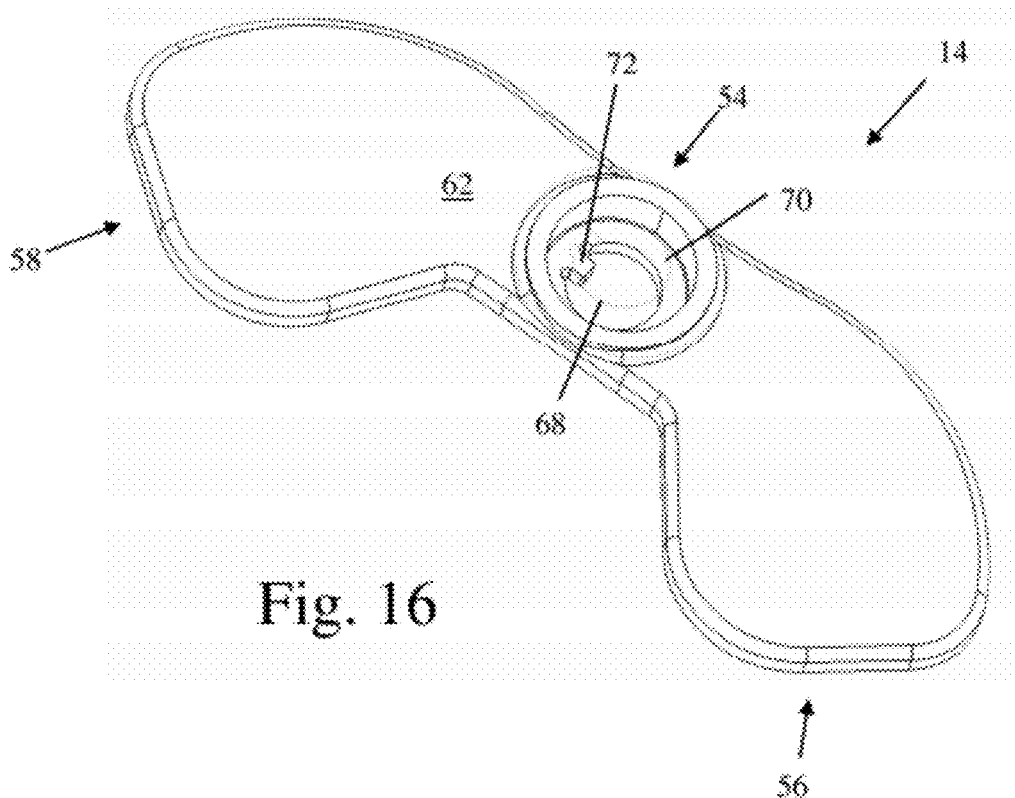
FIGS. 16-17 are top and bottom perspective views, respectively, of the second plate of FIG. 14.
Figure 17:
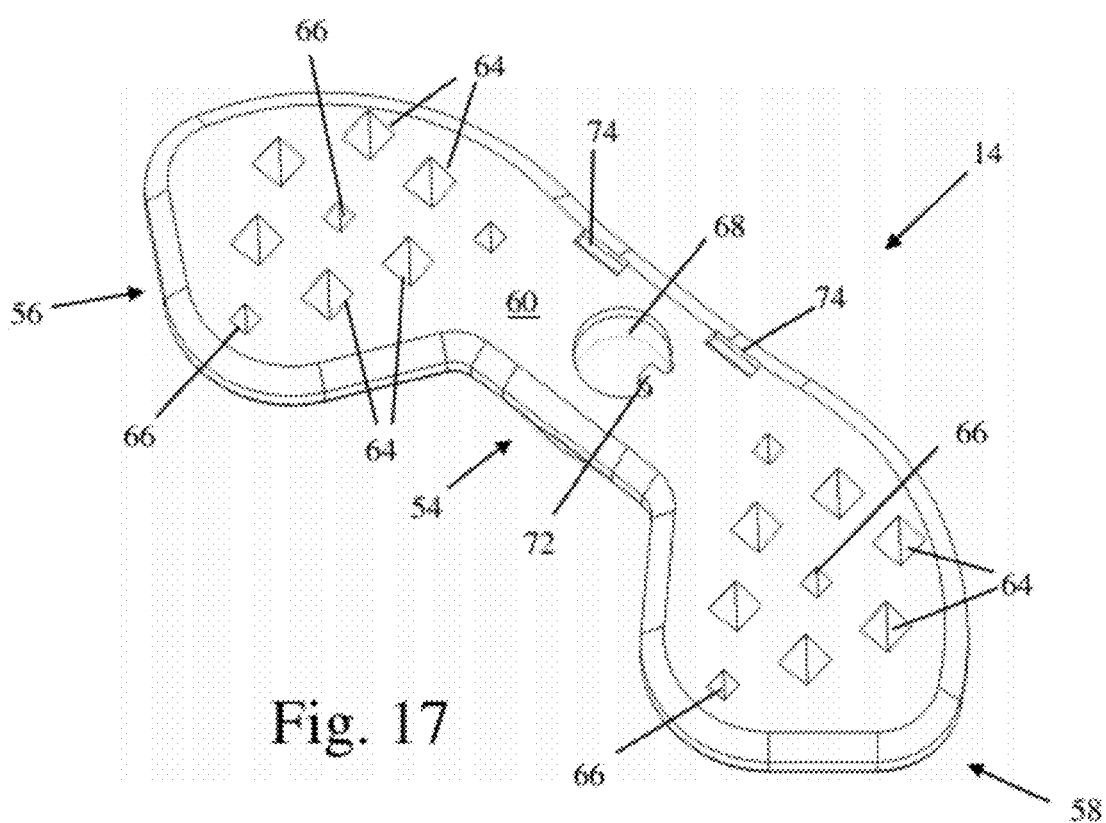

Referring to FIGS. 14-17, the second plate 14 includes similar general features as the first plate 12. The second plate 14 includes a central body portion 54 extending between end portions 56, 58. The second plate 14 further includes a first surface 60 dimensioned to face medially, or toward the first plate 12 when assembled and a second surface 62 dimensioned to face laterally, or away from the first plate 12 when assembled. The central body portion 54 has a generally curved perimeter and (as best viewed in FIGS. 14-15) has a width less than the width of the end portions 56, 58. The increased width of the end portions 56, 58 is designed to present a relatively large footprint on the adjacent spinous processes SP1, SP2, which helps in establishing a robust engagement therewith while avoiding protrusion beyond the spinous processes SP1, SP2. Although generally "hook" shaped in the embodiment shown, one of ordinary skill in the art will appreciate that the end portions 56, 58 may be provided in any number of suitable shapes including but not limited to generally rectangular, generally triangular, and generally rounded. As shown in FIGS. 15 and 17, this engagement may be augmented through the use of a plurality of major and minor spike elements 64, 66 disposed on the medial facing surface of the end portions 56, 58. These spike elements 64, 66 are designed to become embedded in the lateral surface of the spinous processes SP1, SP2 when the spinous process fixation system 10 is compressed in place as shown in FIGS. 1-3. The spike elements 64, 66 are provided in an arrangement complimentary to that of the spike elements 42, 44 of the first plate 12 to increase purchase within the spinous process bone. For example, when the first and second plates 12, 14 are attached to the bone as shown in FIG. 1, major spike elements 42 on first plate 12 will be aligned with minor spike elements 66 on second plate 14, and major spike elements 64 on second plate 14 will be aligned with minor spike elements 44 on first plate 12 so as to minimize the potential for opposing spike elements to contact one another when fully inserted. If this were to happen, the overall purchase of the spike elements within the bone may be reduced, leading to an unstable construct. Providing complementary opposing major and minor spike elements as shown and described herein by example minimizes this risk of "meeting in the middle" of the spinous process bone by ensuring spike elements of differing sizes are inserted into the bone opposite one another. This leads to a more stable construct.

The second plate 14 includes a central aperture 68 dimensioned to receive a distal end of the coupling element 16 as shown in FIGS. 1-3. More specifically, as best viewed in FIGS. 14 and 16, the central aperture 68 is included within a recess 70 formed within the second surface 62 of the second plate 14. The recess 70 is dimensioned to receive the assembled locking assembly 18. More specifically, as will be described in further detail below, the recess 70 is dimensioned to receive the locking element 22, a compression member 24, a portion of the locking cap 26, and at least a portion of the lock nut 28. As will be described in greater detail below, the ridged engagement between the coupling element 16 and the locking element 22 allows the first plate 12 to be coupled to the second plate 14. The second plate 14, according to one embodiment, includes a rectangular boss anti-rotation feature 72. The anti-rotation feature 72 is dimensioned to be received with a corresponding elongated recess 130 (FIG. 35) in coupling element 16. This feature limits and/or prevents the rotation of the first plate 12 and second plate 14 relative to each other about the axis of the coupling element 16 before, during, and after implantation. The second plate 14 further includes a pair of elongated recesses 74 formed within the first surface 60 and positioned on either side of the central aperture 68. Each elongated recess 74 is dimensioned to receive an extension element of an insertion tool, for example such as inserter 400 shown and described below in relation to FIGS. 52-56. The insertion tool may be used to hold and manipulate the second plate 14 as needed to properly position it on the desired spinous processes SP1, SP2.

The second plate 14 may be constructed from any of a variety to suitable materials without departing from the scope of the invention, including but not limited to titanium, polymeric materials (e.g. plastics) carbon fiber, and/or any other biologically acceptable material. The second plate 14 may also be provided having any number of suitable dimensions without departing from the scope of the invention. For example, according to one embodiment, the width of the central body 54 portion may range from 5 mm to 20 mm, the width of the end portions 56, 58 may range from 7.5 mm to 25 mm, the length of the central body portion 54 may range from 1 mm to 65 mm, the length of the end portions 56, 58 may range from 7.5 mm to 25 mm, and the thickness of the second plate 14 may range from 1.5 mm to 15 mm. It will be appreciated, however, that these dimensions are provided as examples of those that may be employed with the spinous process fixation system 10 of the present invention and any number of suitable modifications may be made depending upon a variety of factors without departing from the scope of the invention.

Figure 18:
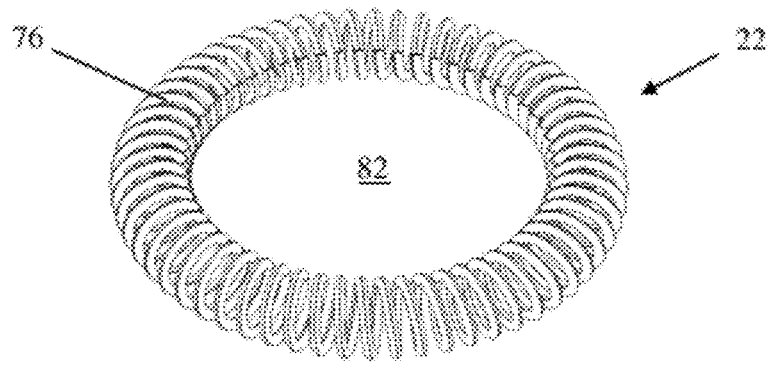
FIGS. 18-20 are perspective, top plan, and side views, respectively, of an example of a locking element forming part of the spinous process fixation system of FIG. 4.
Figure 19:
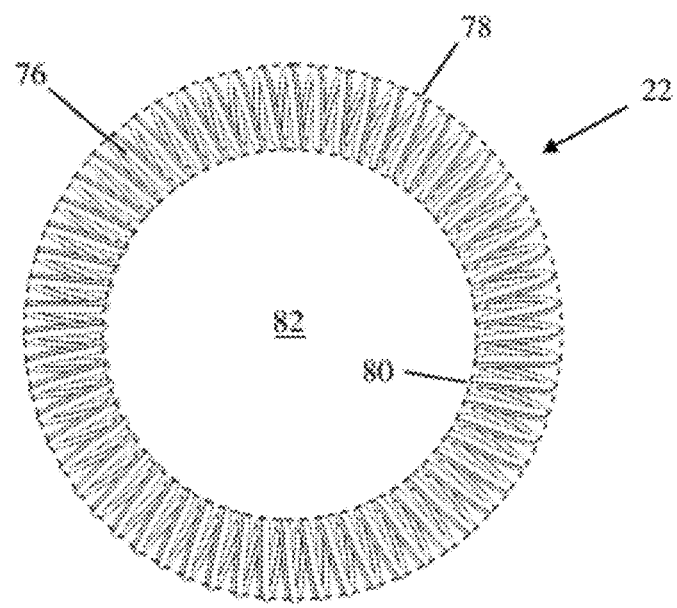
Figure 20:
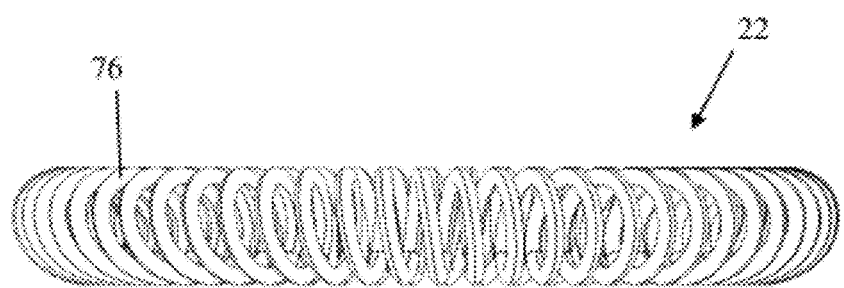

The specific features of the locking assembly 18 will now be described with reference to FIGS. 18-29. FIGS. 18-20 illustrate one example of a locking element 22 forming part of the locking assembly 18 according to one embodiment of the present invention. By way of example only, locking element 22 is provided as a generally circular canted coil ring member 76 dimensioned to be received within the recess 70 of the second plate 14. The locking element 22 may be defined as having an outer circumference 78, an inner circumference 80 and an aperture 82 bounded by the inner circumference 80. Due to the canted coil nature of the locking element 22, each of the circumferences 78, 80 are independently variable. For example, when inserted into the recess 70 of second plate 14, the outer circumference 78 may correspond to the rigid circumference of the recess 70. Upon insertion of a coupling element 16 through aperture 82, the inner circumference 80 may expand to accommodate passage of the ridges 134 of the coupling element 16 (described in further detail below). This expansion of the inner circumference 80 occurs independently from the outer circumference 78 (for example unlike what would occur with a solid snap ring), and thus may occur without any expansion of the outer circumference 78, which is prevented from expanding by the limits of the recess 70 and compression member 24. This independent expansion of the inner circumference 80 occurs due to the canted nature of the coils (best viewed in FIG. 20) in that the individual coils forming the locking element 22 will in effect be forced closer together, or "flattened" against adjacent coils, by the compression cap 24, causing the inner circumference 80 to become smaller. Specifically, the inner edges of the coils (forming the inner circumference 80) will tend to move in one direction, while the outer edges of the coils (forming the outer circumference 78) will remain stationary, causing no change in the outer circumference 78. It will be understood that "flattened" as used herein is not intended to describe the coils as assuming a planar configuration, but rather that the coils are compressed against one another in a generally angled state. Upon insertion of the coupling element 16, the force exerted by the ridges 134 does not cause purely radial expansion of the locking element 22, but rather the elastic nature of the coils allow the individual coils to be deformed, thus temporarily expanding the inner circumference 80 to allow for passage of the coupling element 16 therethrough.

By way of example only, the locking element 22 may be have any number suitable sizes, both of the individual rings and of the outer and inner circumferences 78, 80, respectively. The locking element 22 may be formed of any suitable biocompatible material, including but not limited to metal. According to a preferred embodiment, in use the locking element 22 is provided within recess 70 of second plate 14 prior to insertion during the surgical procedure, as part of the locking assembly 18.

Figure 21:
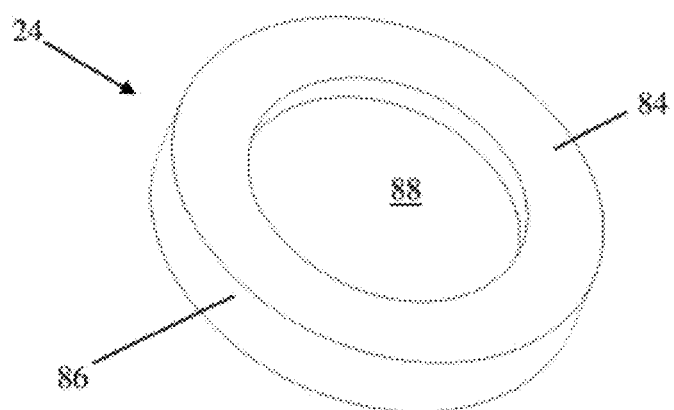
FIGS. 21-23 are top perspective, bottom perspective, and side cross-sectional views, respectively, of an example of a compression member forming part of the spinous process fixation system of FIG. 4.
Figure 22:
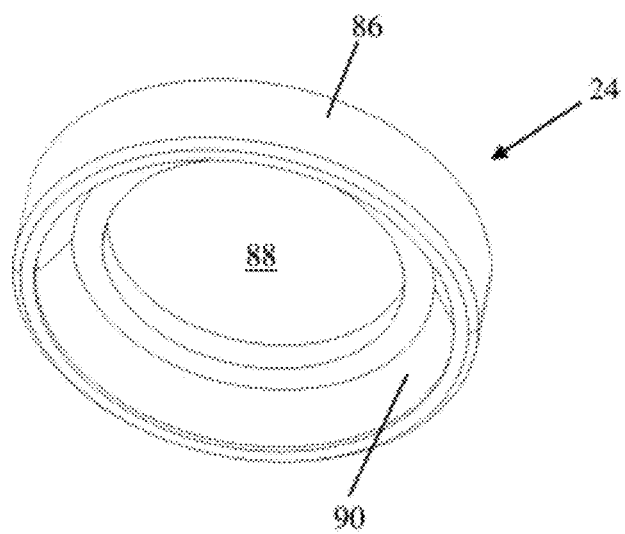
Figure 23:
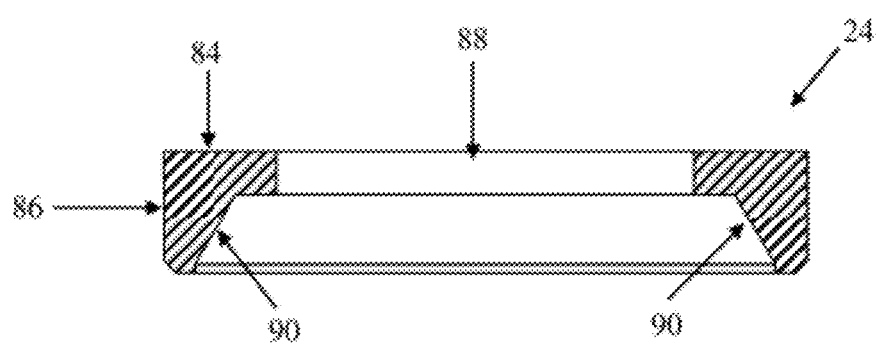

FIGS. 21-23 illustrate one example of a compression cap 24 forming part of the locking assembly 18 according to one embodiment of the present invention. By way of example only, the compression cap 24 is an annular member dimensioned to be received within the recess 70 of second plate 14. The compression cap 24 has a generally planar top surface 84, a smooth annular side surface 86, and a central aperture 88 formed in the middle of the compression cap 24. The compression cap 24 further includes a conical surface 90 forming at least a portion of the interior of the central aperture 88. The compression cap 24 is sized such that the annular side surface 86 snugly engages the interior of the recess 70 of the second plate 14. The aperture 88 is sized to allow passage of the coupling element therethrough. The conical surface 90 is dimensioned to engage the locking element 22 and urge the canted coil ring member 76 to "flatten" in one direction, which allows for insertion of the coupling element 16 therethrough while preventing the removal of the coupling element 16 in the opposite direction. This essentially allows for unidirectional translation of the coupling element 16 relative to the second plate 14 while the locking assembly 18 is in place.

Figure 24:
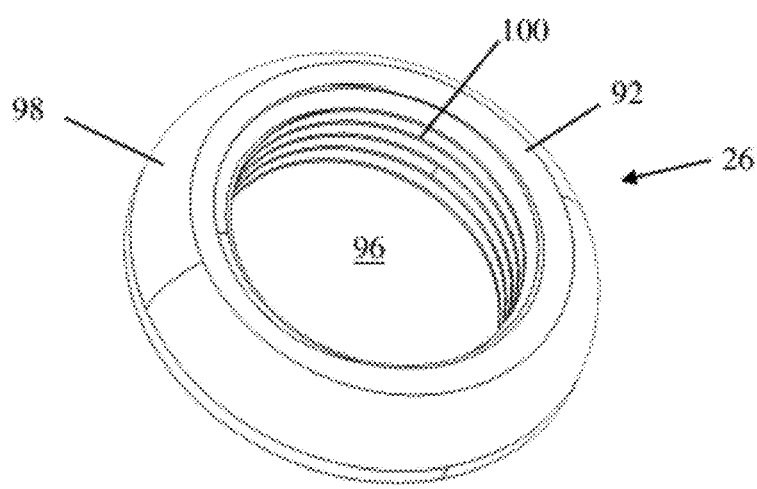
FIGS. 24-26 are top perspective, bottom perspective, and side plan views, respectively, of an example of a locking cap forming part of the spinous process fixation system of FIG. 4.
Figure 25:
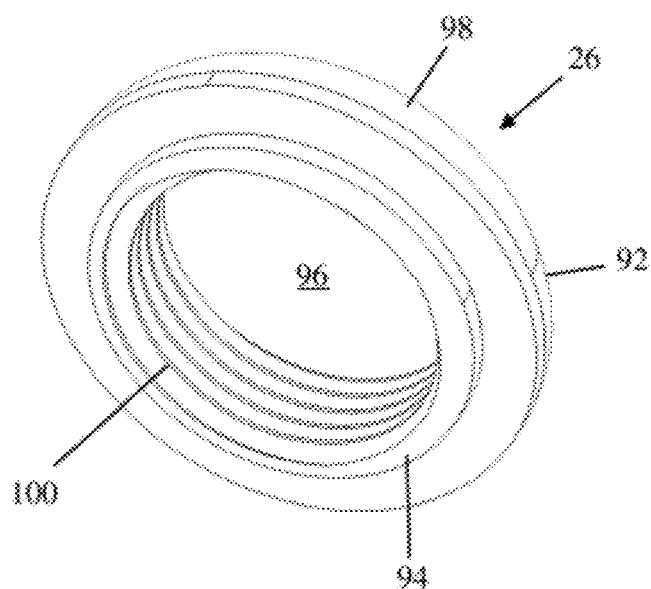
Figure 26:
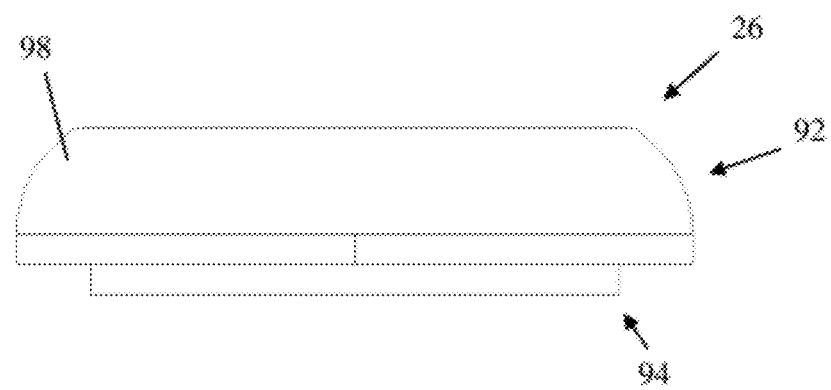

FIGS. 24-26 illustrate one example of a locking cap 26 forming part of the locking assembly 18 according to the present invention. By way of example only, the locking cap 26 is an annular member having an upper portion 92, a lower portion 94, and a central aperture 96 extending therethrough. The upper portion 92 includes a generally rounded first surface 98 which forms part of the outer perimeter of the spinous process fixation system 10. The rounded nature of the first surface 98 helps ensure smooth external surfaces that are unlikely to "catch" on neighboring body tissue. The lower portion 94 has a circumference that this less than the circumference of the upper portion 92, and generally corresponding to the circumference of the recess 70 of the second plate 14. This ensures that the lower portion 94 is snugly received within at least a portion of the recess 70. The central aperture 96 includes a threaded region 100 dimensioned to interact with the threaded region 108 on the lock nut 28, described in further detail below.

Figure 27:
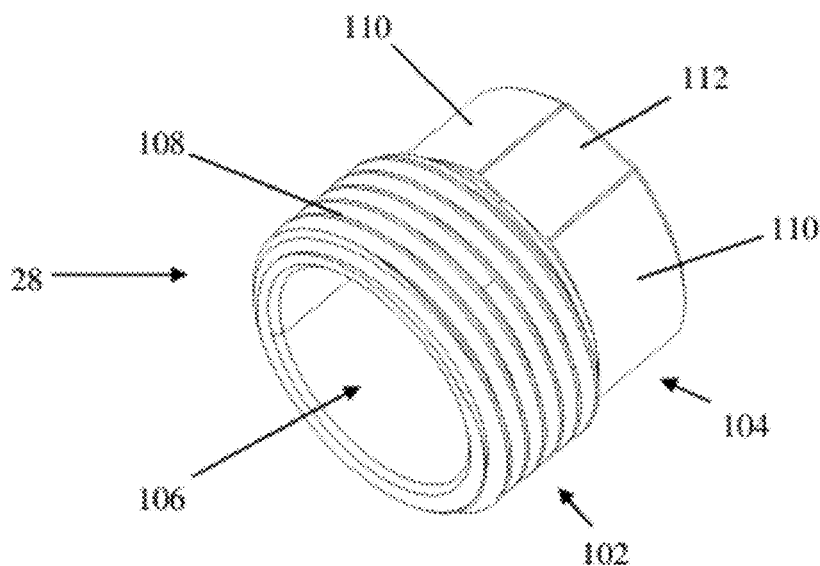
FIGS. 27-29 are perspective, plan, and perspective views, respectively, of an example of a lock nut forming part of the spinous process fixation system of FIG. 4.
Figure 28:
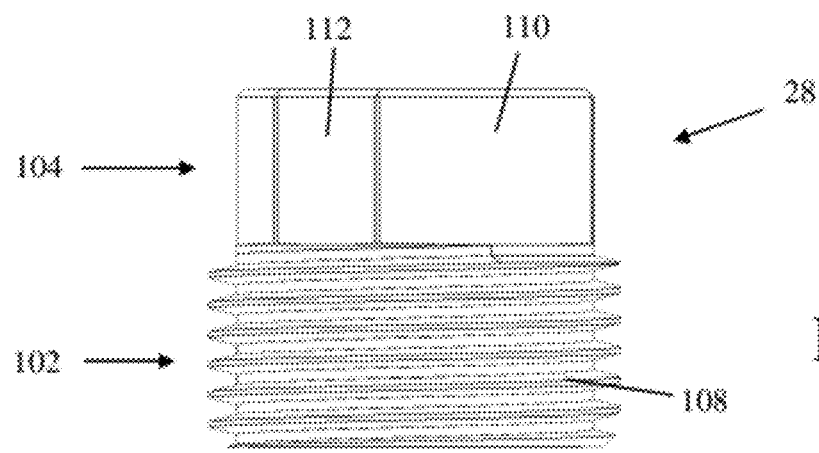
Figure 29:
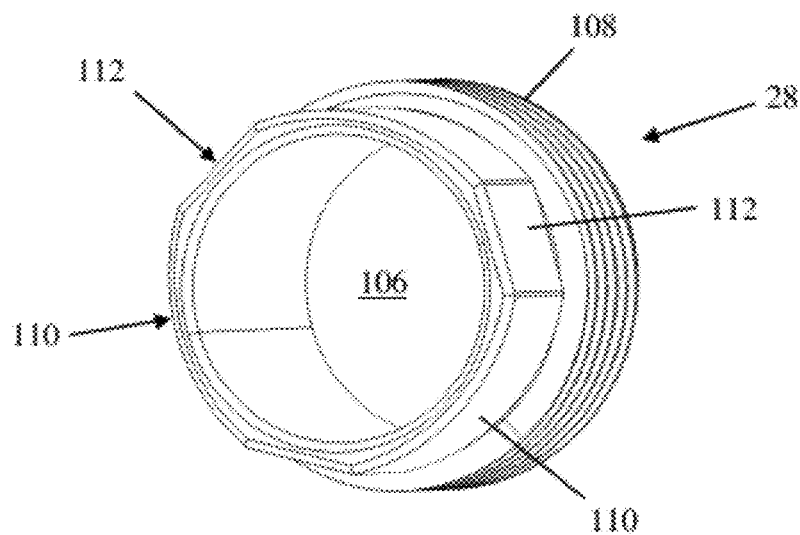
Figure 30:
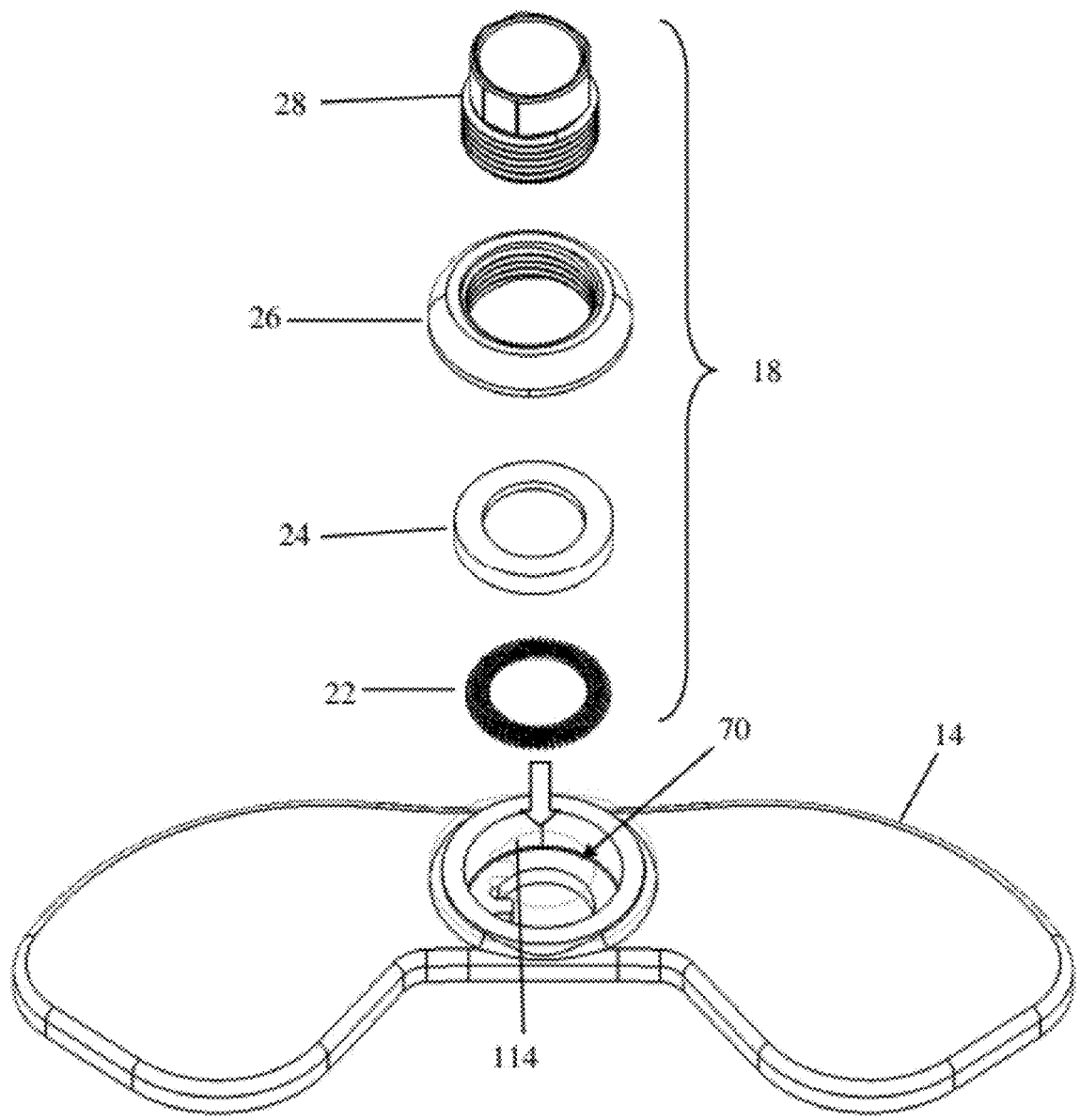
FIGS. 30-34 are various views of a process of assembling a second plate assembly forming part of the spinous process fixation system of FIG. 4.

FIGS. 27-29 illustrate one example of a lock nut 28 forming part of the locking assembly 18 according to the present invention. By way of example only, the lock nut 28 includes a lower portion 102 comprising a distal end, an upper portion 104 comprising a proximal end, and a central aperture 106 extending through the lock nut 28 from upper portion 104 to the lower portion 102. The lower portion 102 is generally cylindrical and includes a threaded region 108 dimensioned to threadedly engage with the threaded region 100 on the locking cap 26. Described in further detail below, this threaded engagement ensures sufficient force is being applied to the compression cap 24 to maintain the locking element 22 in a "flattened" state. The upper portion 104 includes a plurality of generally curved surfaces 110 interrupted by a plurality of generally planar surface 112 to form an engagement region for a removal tool (not shown).

When fully assembled, the lower portion 102 of the lock nut 28 will be almost fully, if not fully received within the central aperture 96 of the locking cap 26. The upper portion 204 will thus be exposed to the exterior of the construct. The lock nut 28 is an essential feature for the removal and/or repositioning of the spinous process fixation system 10. When the lock nut 28 is fully engaged, the coupling element 16 will not be able to be removed from the system 10 due to the "flattened" state of the locking element 22. However, to disengage the locking element 22, the lock nut 28 is rotated in a counter-clockwise direction (after engaging the upper portion 104 with an appropriate removal tool) to back the lock nut 28 out of the central aperture 96 of the locking cap 26. This in turn releases the force applied to the compression cap 24, which in turn allows the locking element 22 to return to a relaxed position. In the "relaxed" state, the locking element 22 allows for bi-directional translation of the coupling element 16 relative to the second plate 14, thus allowing for removal of the coupling element 16. This may be necessary, for example, should the surgeon determine that the spinous process fixation system 10 needs to be adjusted or removed altogether.

Figure 31:
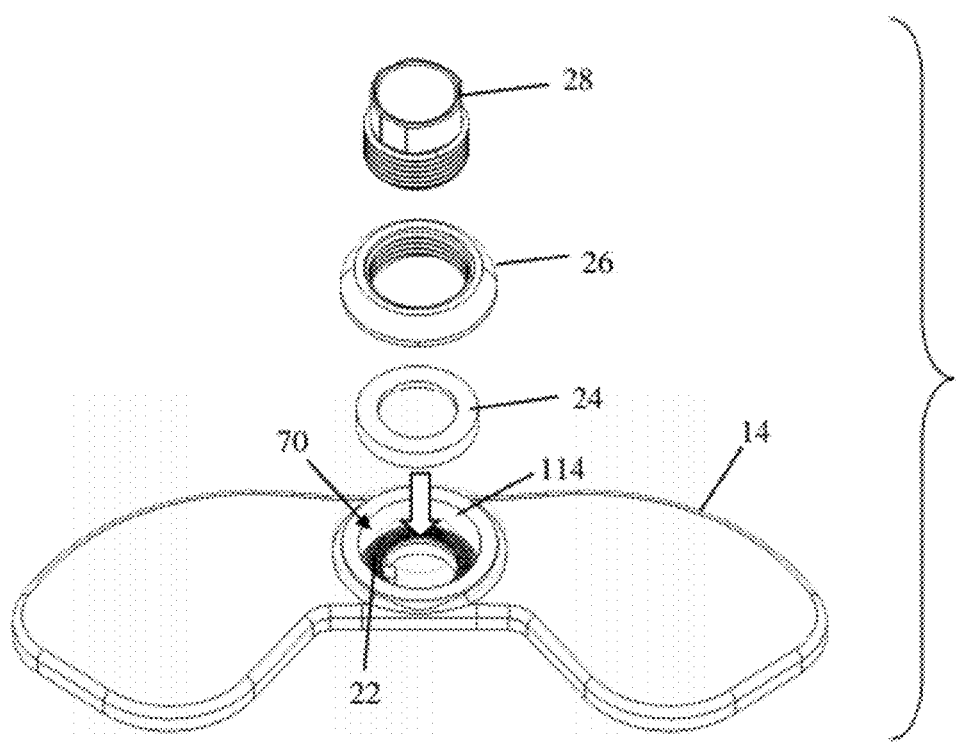
Figure 32:
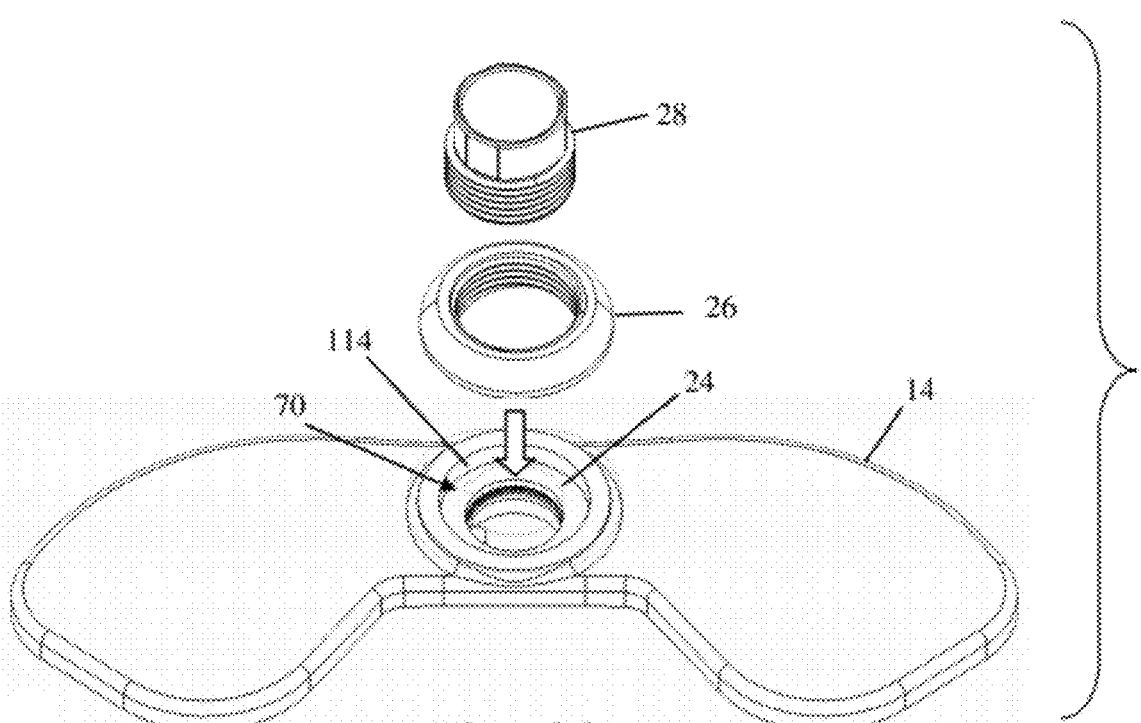

FIGS. 30-34 illustrate the sequential assembly of the locking assembly 18 and the second plate 14. To assemble the locking assembly 18 within the second plate 14, the first step is to place the locking element 22 within the recess 70 of the second plate 14, as shown in FIG. 31. When in a "relaxed" state, the outer circumference 78 (FIG. 19) of the locking element 22 should be comfortably flush against the inner annular wall 114 of the recess 70. Referring to FIG. 32, the second step is the insertion of the compression cap 24 into the recess 70. As with the locking element 22, the annular side surface 86 of the compression cap 24 should have a circumference approximately corresponding to the circumference of the recess 70 such that the compression cap 24 is comfortably flush against the inner annular wall 114 of the recess 70. At this point the conical surface 90 (FIG. 20) of the compression cap 24 is resting atop the locking element 22.

Figure 33:
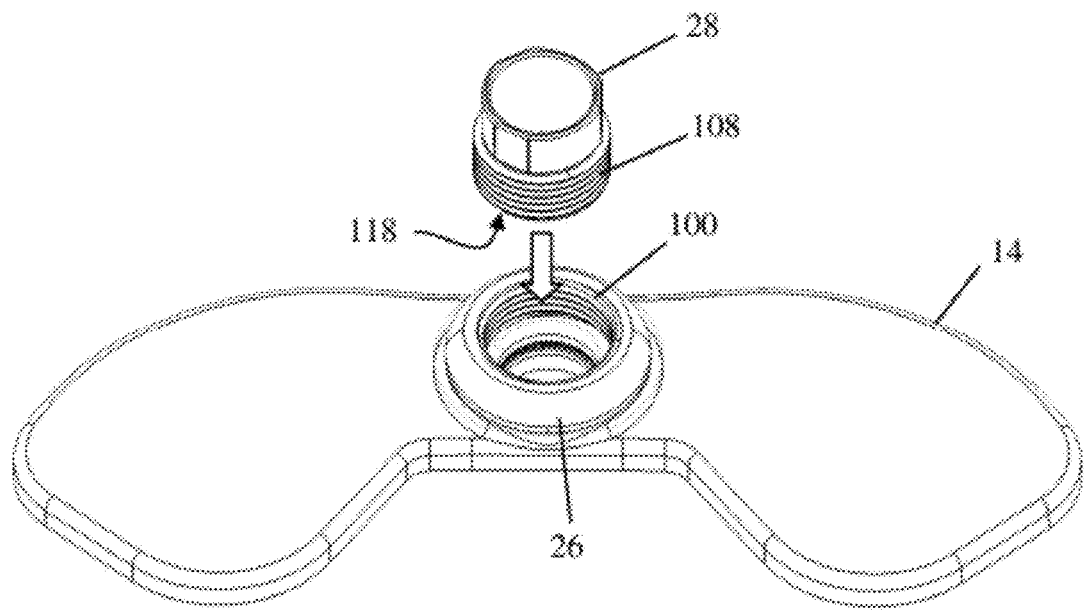

Now referring to FIG. 33, the third step is the placement of the locking cap 26 over the recess 70. The locking cap 26 is dimensioned such that the lower portion 94 is comfortably flush against the inner annular wall 114 of the recess 70, and the upper portion 98 sits outside the recess 70. It is important to note that the lower portion 94 does not contact the compression cap 24, but rather there is a space 116 (FIG. 38) between the lower portion 94 and the compression cap 24. This space enables the compression cap 24 to be "loosened" such that the locking element 22 returns to its "relaxed" state to enable removal of the coupling element 16. The locking cap 26 may be rigidly attached to the second plate 14, for example through adhesive, welding, or a threaded engagement (not shown). Alternatively, the locking cap 26 may be provided with a more temporary engagement feature, for example such as a friction fit, to secure the locking cap 26 to the second plate 14. Securement of the locking cap 26 to the second plate 14 ensures that the compression cap 24 and locking element 22 remain within the recess 70 during removal of the coupling element 16 and potential repositioning of the spinous process fixation system 10.

Figure 34:
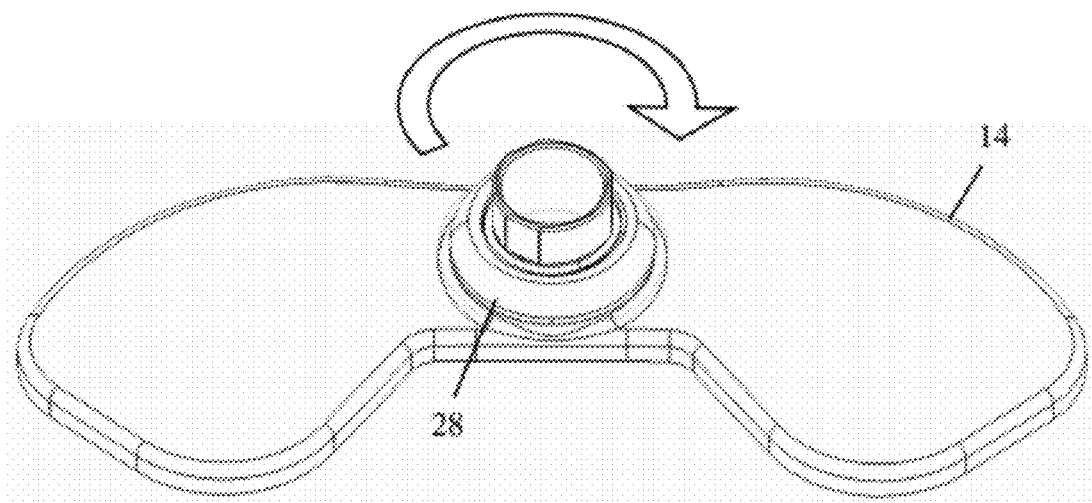

Referring to FIG. 34, insertion of the lock nut 28 is the final step in the coupling of the locking assembly 18 with the second plate 14. As previously mentioned, the threaded region 108 of the lock nut 28 interacts with the threaded region 100 of the locking cap 26 to enable the lock nut 28 to apply a force to the compression cap 24. To do this, the lock nut 28 is rotated in a clockwise direction and threaded onto the locking cap 26 until the distal end region 118 (FIG. 38) contacts the compression cap 24. Further clockwise rotation of the lock nut 28 will exert a force on the compression cap 24 and cause the locking element 22 to change from a "relaxed" position to a "flattened" position and thus decreasing the inner circumference 80 of the locking element 22. At this point, the second plate 14 is prepared to receive the coupling element 16.

FIGS. 35-37 illustrate an example of a coupling element 16 according to one embodiment of the present invention. As shown, the coupling element 16 is a ridged bolt having a "truncated spherical" shaped head 120 and a shaft 122 extending therefrom with a ridged portion 124. The shaft 122 of the coupling element 16 is dimensioned to be passed through the central aperture 46 of the first plate 12 and then onward through the central aperture 68 of the second plate 14 to the point where the ridged portion 124 matingly engages the locking element 22 within the recess 70 of the second plate 14. As this occurs, the truncated spherical head 120 of the coupling element 16 will be advanced into the central aperture 46 of the first plate 12. The truncated spherical head 120 has a larger diameter than the inner periphery of the central aperture 46 such that the head 120 cannot pass through the aperture 46 but rather cooperates in a "keyed" fashion with the central aperture 46. Specifically, straight sides 126 and semi-spherical portions 128 of the head 120 cooperate with the straight sides 48 and semi-spherical end regions 50, respectively, of the aperture 46. In one embodiment, central aperture 46 may have an oblong-shaped opening to allow for temporary pivoting of the coupling element 16 prior to final tightening of the spinous process fixation system 10. The coupling element 16 will thus couple the first plate 12 to the second plate 14 as the bolt 16 is advanced axially into engagement with the locking element 22 within the second plate 14. As explained in greater detail below, the locking element 22 is dimensioned such that the ridges 124 of the coupling element 16 pass relatively easily through the aperture 68 towards the second surface 62 of the second plate 14 but relatively difficulty in the opposite direction. In this manner, the first plate 12 and second plate 14 will be coupled in a secure manner on adjacent sides of the spinous processes SP1, SP2. Any of a variety of tools may be used to remove the coupling element 16 from engagement with the locking element 22 so as to disengage the first plate 12 from the second plate 14.

Initially, the coupling element 16 may be provided as being rigidly (and immovably) attached to the second plate 14. For example, this may be accomplished by using at least one, and preferably two, spot welds 30 (FIG. 5) to temporarily rigidly attach the coupling element 16 to the first plate 12. Once the first plate 12 is placed in position against the first and second spinous processes SP1, SP2, the spot welds 30 may be broken, allowing the coupling element 16 to pivot freely (and unattached) within the central aperture 46 due to the interaction between the truncated spherical shaped head 120 and semi-spherical end regions 50 of the central aperture 46 (FIG. 11).

The coupling element 16 further includes an elongated recess 130 extending substantially the length of the shaft 122 and terminating at the distal end 132 of the coupling element 16. The elongated recess 130. This elongated recess 130 has a shape dimension generally corresponding to the shape of the anti-rotation feature 72 of the second plate 14. As previously mentioned this feature limits and/or prevents the rotation of the first plate 12 and second plate 14 relative to each other about the axis of the coupling element 16 before, during, and after implantation. The elongated nature of the recess 130 allows for translation of the anti-rotation feature 72 within the recess 130 while the coupling element 16 is advanced or retreated from second plate 14.

Referring now to FIG. 37, the ridged portion 124 of the shaft 122 includes a plurality of ridges 134 that interact with the locking element 22 to control the translation of the coupling element 16. More specifically, when the locking assembly 18 is in position, the ridges 134 and coupling element 22 cooperate to allow only unidirectional translation of the coupling element 16 (e.g. in a medial direction to effect compression of the first and second plates 12, 14 against the spinous processes SP1, SP2). The shape of the ridges 134 facilitate this unidirectional feature. Specifically, each ridge 134 has a leading surface 136 that is outwardly beveled (toward head 120) from the shaft 122. Each ridge 134 further has a trailing upwardly facing surface 138 that extends generally perpendicularly from the shaft 122 to a location where it meets the leading surface 136. It is important to note that the trailing surface may not be inwardly beveled toward the head 120 because then the unidirectional translation functionality of the construct may be diminished. The ridges 134 are spaced apart along the shaft 122 at a predetermined distance generally corresponding to the width of the locking element 22 such that a portion of the locking element 22 will occupy a space between two adjacent ridges 134 upon final tightening of the spinous process fixation system 10.

The coupling element 16 may be constructed from any of a variety of suitable materials without departing from the scope of the invention, including but not limited to titanium, polymeric materials (e.g. plastics) carbon fiber, and/or any other biologically acceptable material. The coupling element 16 may also be provided having any number of suitable dimensions without departing from the scope of the invention. For example, according to one embodiment, the width of the coupling element 16 may range from 3 mm to 10 mm, the length of the coupling element 16 may range from 15 mm to 50 mm, and the ridged portion 124 may range from 5 mm to 47 mm. It will be appreciated, however, that these dimensions are provided as examples of those that may be employed with the spinous process fixation system 10 of the present invention and any number of suitable modifications may be made depending upon a variety of factors without departing from the scope of the invention.

Figure 38:
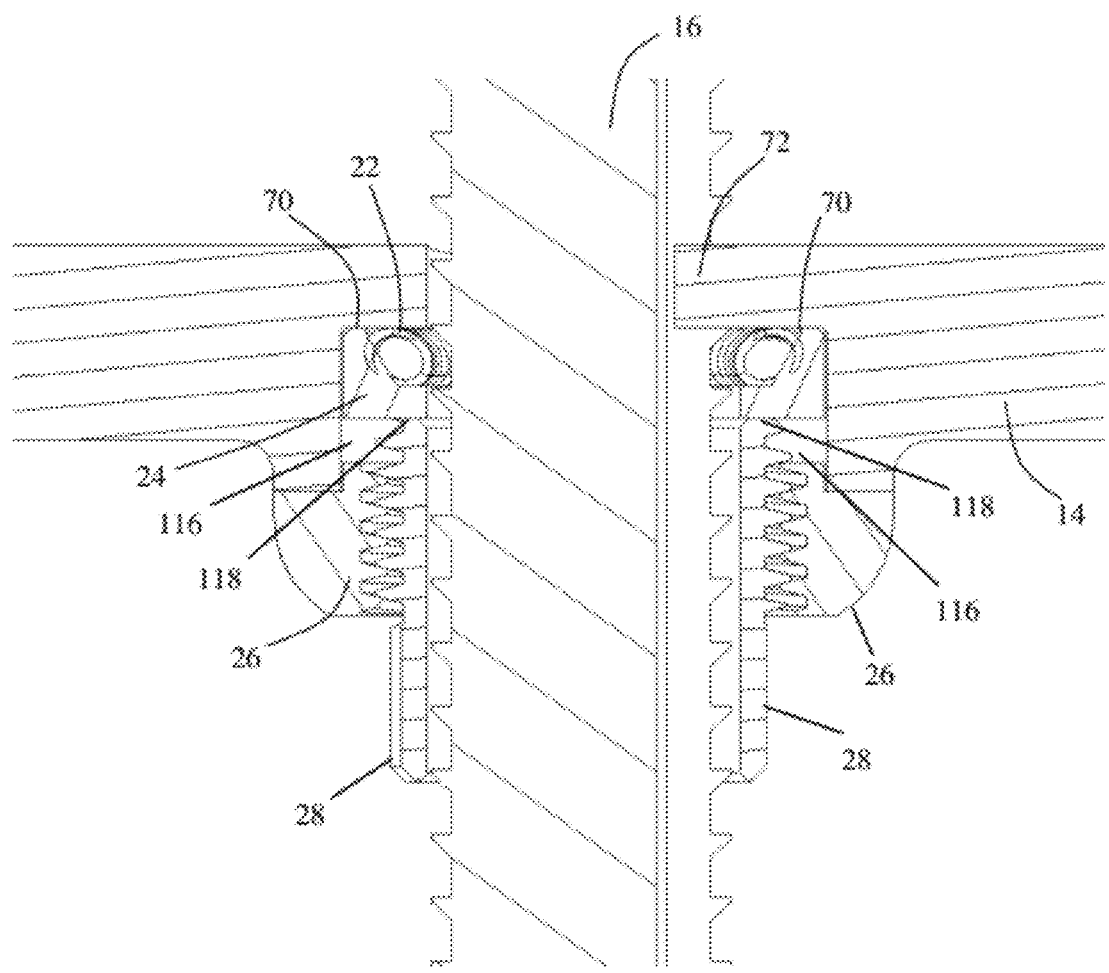
FIG. 38 is a cross-sectional view of the second plate assembly of FIG. 34 coupled to the coupling element of FIG. 35.
Figure 39:
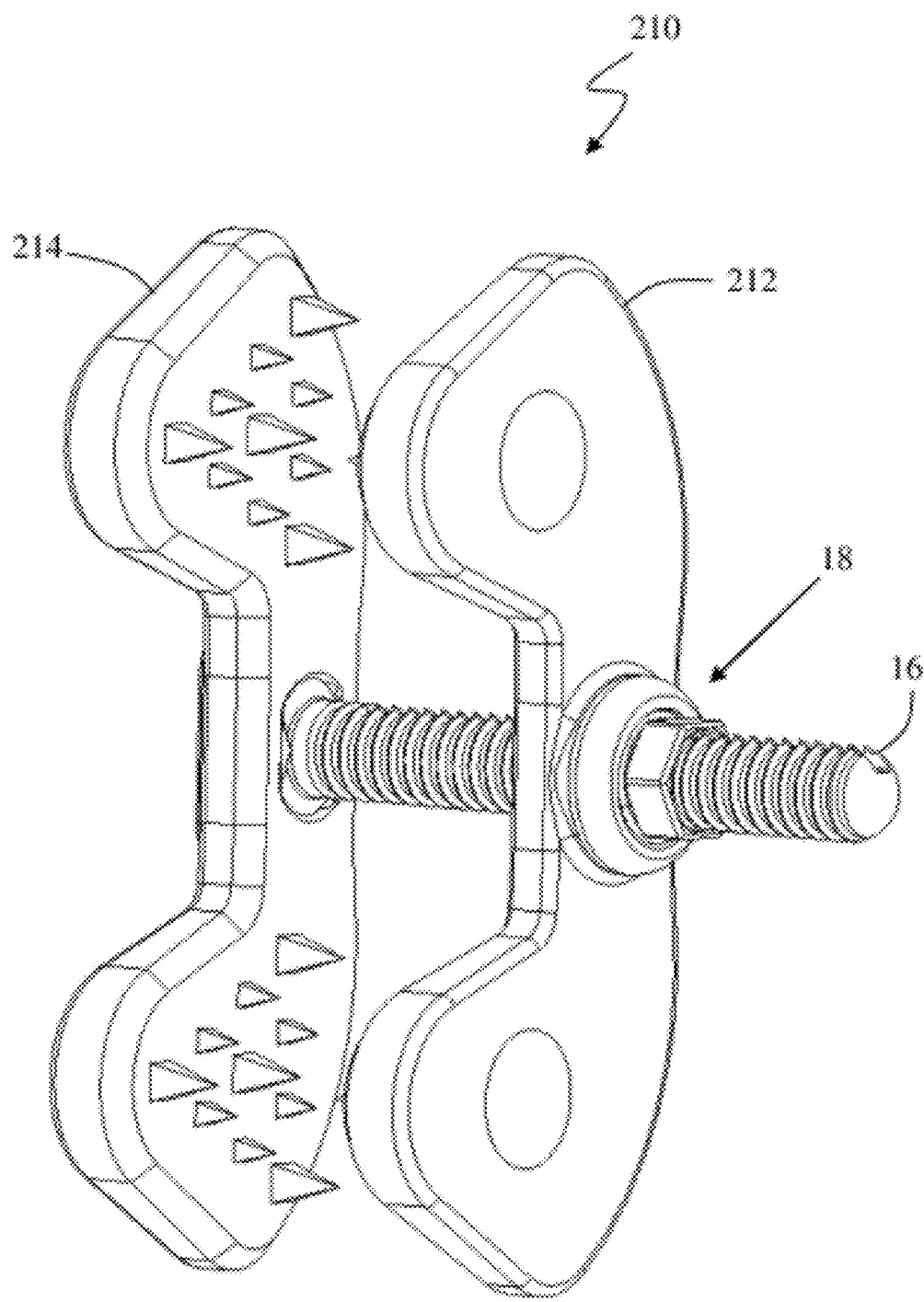
FIG. 39 is a perspective view of an example of a spinous process fixation system according to a second embodiment of the present invention.

FIG. 38 is a cross-sectional view of a portion of the second plate 14 upon coupling to an assembled locking element 18 and insertion of the coupling element 16. As shown in FIG. 38, when compression member 24 is positioned in place, locking element 22 is deformed such that a portion of the inner circumference 80 extends into the central aperture 68 of the second plate 14. This will help foster engagement with the ridges 134 of the coupling element 16. As the coupling element 16 is inserted through locking element 22, the inner circumference 80 is deformed as described above and as shown by example in FIG. 38, allowing for essentially unidirectional movement of the coupling element 16 through the locking element 22. Locking cap 26 and lock nut 28 are threadedly engaged to each other and attached to second plate 14 in order to secure the compression member 24 and locking element 22 in place, with sufficient force on the locking element 22 to create the desired deformity described above. In the event one or more of the first and second plates 12, 14 need to be repositioned (i.e. the coupling element 16 needs to be removed or disengaged), the lock nut 28 and locking cap 26 need only to be loosened and/or removed. This will release the force applied to the compression cap 26, which will in turn cause the locking element 22 to assume a relaxed state. Once in the relaxed state, the locking element 22 will allow for bi-directional movement of the coupling element 16. This is due partially to the fact that once the compression cap 26 is relaxed and/or removed, the locking element 22 may retreat further into recess 70, and partially to the canted coil nature of the locking element 22 as described above.

FIGS. 39-43 illustrate an example of a spinous process fixation system 210 according to a second embodiment of the present invention. Spinous process fixation system 210 is substantially similar to the spinous process fixation system 10 described above, with the only difference being in the first and second plates 212, 214. All other features, including the coupling element 16 and locking assembly 18 (and component parts thereto) are identical to that described above, and thus repeat disclosure has been omitted. It should be understood that any of the components described herein in relation to a specific embodiment of the present invention are interchangeable with any other of the components described in relation to any embodiment. Embodiments disclosed herein are provided by way of example to illustrate all of the features of the present invention without limitation as to the specific combination of features. Consequently, features identical to those previously discussed will be assigned the same reference numbers as set forth above.

Figure 40:
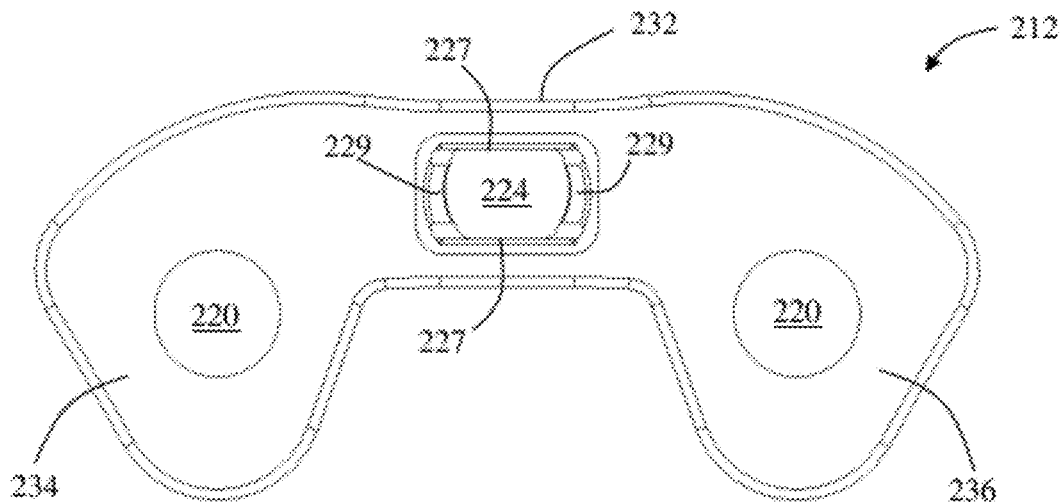
FIGS. 40-41 are top and bottom plan views, respectively, of an example of a first plate forming part of the spinous process fixation system of FIG. 39.
Figure 41:
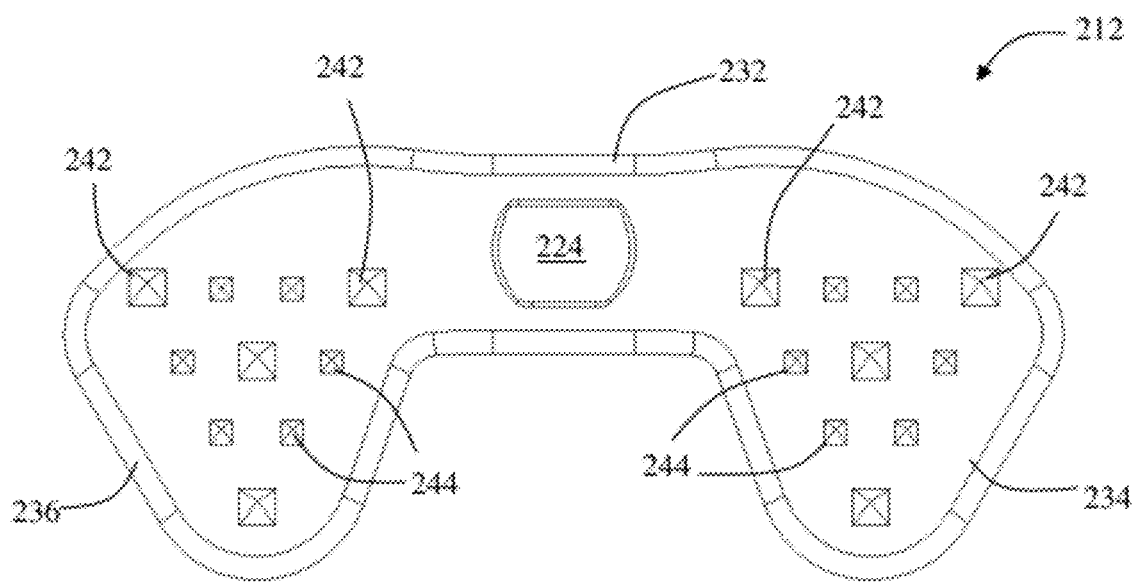

The first plate 212 will now be described with specific reference to FIGS. 40-41. The first plate 212 includes a central body portion 232 extending between a pair of end portions 234, 236. The central body portion 250 may have a generally curved perimeter and has a width less than the width of the end portions 234, 236. The increased width of the end portions 234, 236 is designed to present a relatively large footprint on the adjacent spinous processes SP1, SP2, which helps in establishing a robust engagement therewith while avoiding protrusion beyond the spinous processes SP1, SP2. Although generally "hook" shaped in the embodiment shown, one of ordinary skill in the art will appreciate that the end portions 234, 236 may be provided in any number of suitable shapes including but not limited to generally rectangular, generally triangular, and generally rounded. This engagement may be augmented through the use of a plurality of major and minor spike elements 242, 244, respectively, disposed on the medial facing surface of the end portions 234, 236. These spike elements 242, 244 are designed to become embedded in the lateral surface of the spinous processes SP1, SP2 when the system 210 is compressed in place as shown in FIG. 1. As described in further detail below, the spike elements 242, 244 are provided in an arrangement complimentary to that of the spike elements 264, 266 of the first plate 212 to increase purchase within the spinous process bone.

The first plate 212 includes a central aperture 224 dimensioned to receive a proximal end 120 of the coupling element 16 (FIG. 35). More specifically, the central aperture 224 is a "truncated spherical" recess having straight sides 227 and semi-spherical end regions 229. The straight sides 227 and semi-spherical end regions 229 are dimensioned to receive the generally straight sides 126 and semi-spherical end regions 128 of the head 120 of the coupling element 16 (FIGS. 35-37). The first plate 212 also, according to one embodiment, includes attachment apertures 220 positioned on either side of the central aperture 224. Each aperture 220 is dimensioned to receive an extension element of an insertion tool, for example such as inserter 400 shown and described below in relation to FIGS. 52-56. The insertion tool may be used to hold and manipulate the first plate 212 as needed to properly position it on the desired spinous processes SP1, SP2.

The first plate 212 may be constructed from any of a variety to suitable materials without departing from the scope of the invention, including but not limited to titanium, polymeric materials (e.g. plastics such as poly-ether-ether-ketone) carbon fiber, and/or any other biologically acceptable material. The first plate 212 may also be provided with any number of suitable dimensions without departing from the scope of the invention. For example, according to one embodiment, the width of the central body portion 232 may range from 5 mm to 20 mm, the width of the end portions 234, 236 may range from 7.5 mm to 25 mm, the length of the central body portion 232 may range from 1 mm to 65 mm, the length of the end portions 234, 236 may range from 7.5 mm to 25 mm, and the thickness of the first plate 212 may range from 1.5 mm to 15 mm. It will be appreciated, however, that these dimensions are provided as examples of those that may be employed with the spinous process fixation system 210 of the present invention and any number of suitable modifications may be made depending upon a variety of factors without departing from the scope of the invention.

Figure 42:
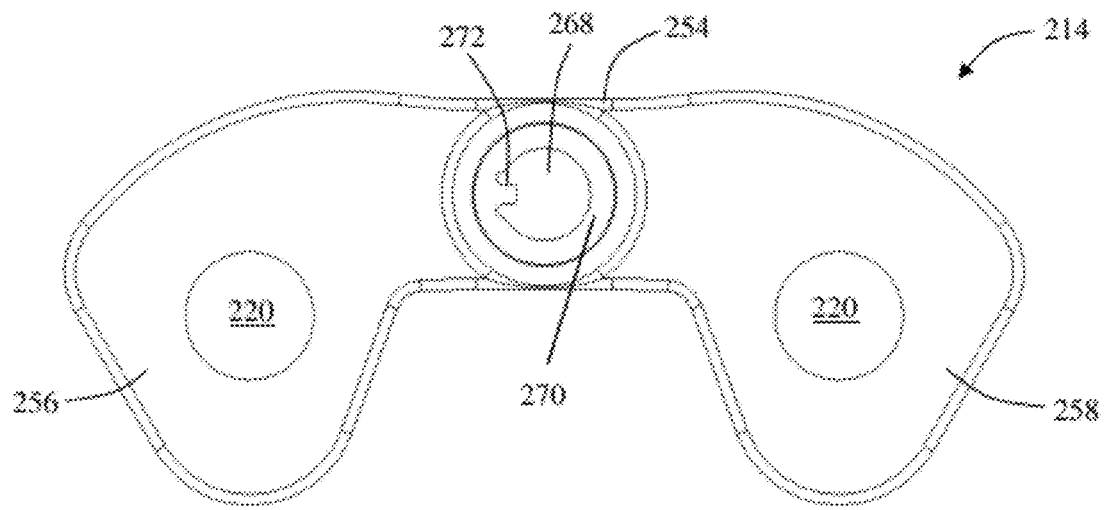
FIGS. 42-43 are top and bottom plan views, respectively, of an example of a second plate forming part of the spinous process fixation system of FIG. 39.
Figure 43:
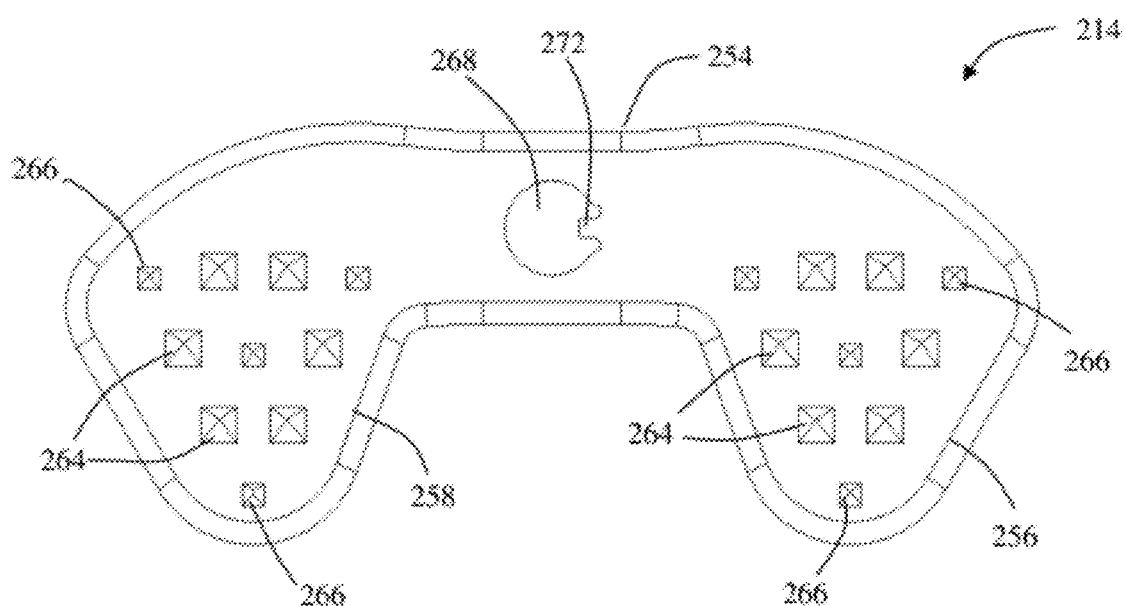
Figure 44:
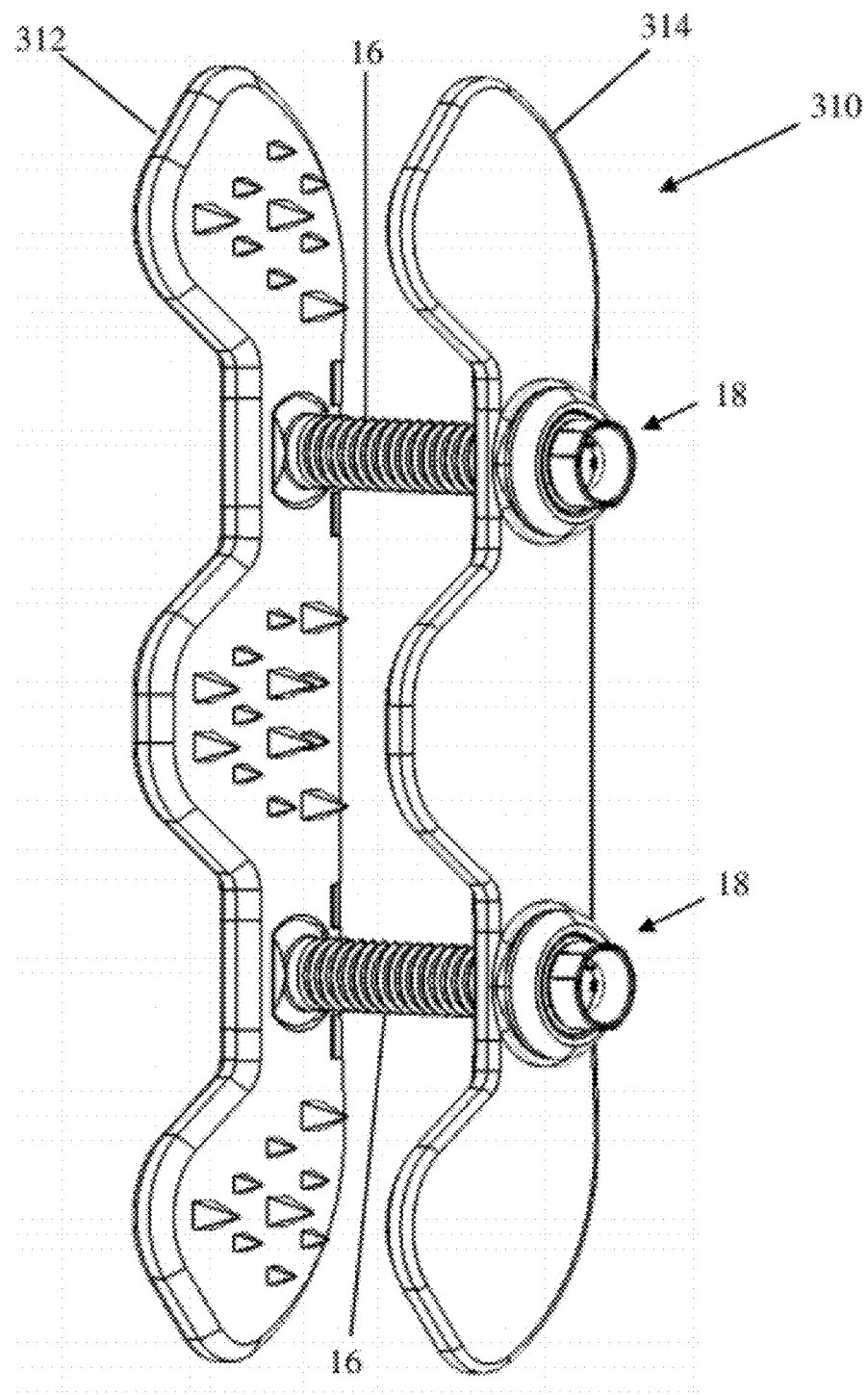
FIGS. 44-45 are perspective views of an example of a spinous process fixation system according to a third embodiment of the present invention.
Figure 45:
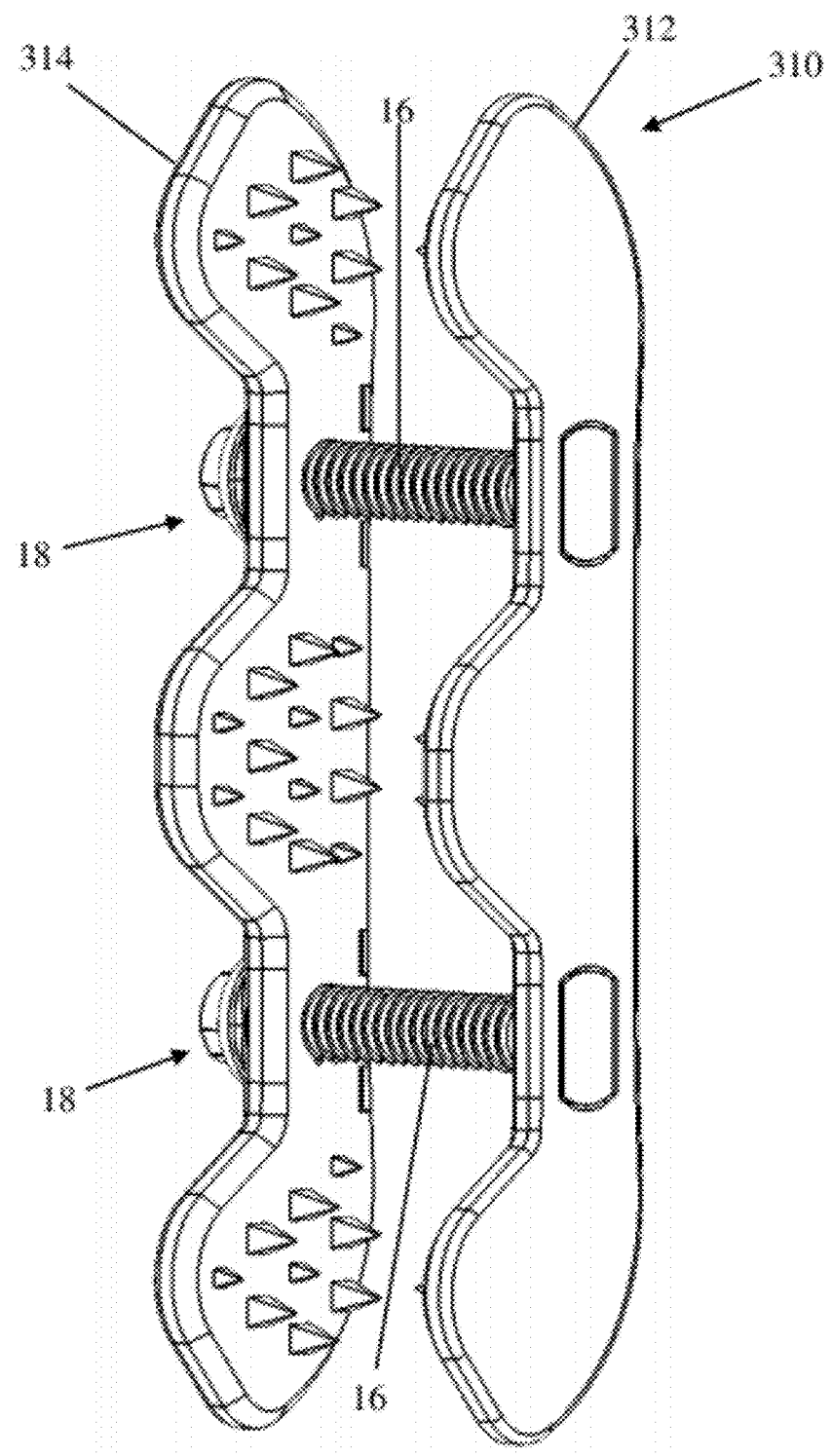

Referring to FIGS. 42-43, the second plate 214 includes similar general features as the first plate 212. The second plate 214 includes a central body portion 254 extending between end portions 256, 258. The second plate 214 further includes a first surface 260 dimensioned to face medially, or toward the first plate 212 when assembled and a second surface 262 dimensioned to face laterally, or away from the first plate 212 when assembled. The central body portion 254 has a generally curved perimeter and has a width less than the width of the end portions 256, 258. The increased width of the end portions 256, 258 is designed to present a relatively large footprint on the adjacent spinous processes SP1, SP2, which helps in establishing a robust engagement therewith while avoiding protrusion beyond the spinous processes SP1, SP2. Although generally "hook" shaped in the embodiment shown, one of ordinary skill in the art will appreciate that the end portions 256, 258 may be provided in any number of suitable shapes including but not limited to generally rectangular, generally triangular, and generally rounded. This engagement may be augmented through the use of a plurality of major and minor spike elements 264, 266 disposed on the medial facing surface of the end portions 256, 258. These spike elements 264, 266 are designed to become embedded in the lateral surface of the spinous processes SP1, SP2 when the spinous process fixation system 210 is compressed in place as shown in FIGS. 1-3. The spike elements 264, 266 are provided in an arrangement complimentary to that of the spike elements 242, 244 of the first plate 212 to increase purchase within the spinous process bone. For example, when the first and second plates 212, 214 are attached to the bone as shown in FIG. 1, major spike elements 242 on first plate 212 will be aligned with minor spike elements 266 on second plate 214, and major spike elements 264 on second plate 214 will be aligned with minor spike elements 244 on first plate 212 so as to minimize the potential for opposing spike elements to contact one another when fully inserted. If this were to happen, the overall purchase of the spike elements within the bone may be reduced, leading to an unstable construct. Providing complementary opposing major and minor spike elements as shown and described herein by example minimizes this risk of "meeting in the middle" of the spinous process bone by ensuring spike elements of differing sizes are inserted into the bone opposite one another. This leads to a more stable construct.

The second plate 214 includes a central aperture 268 dimensioned to receive a distal end of the coupling element 16 as shown in FIGS. 1-3. More specifically, the central aperture 268 is included within a recess 270 formed within the second surface 262 of the second plate 214. The recess 270 is dimensioned to receive the assembled locking assembly 18. More specifically, as described above in relation to spinous process fixation system 10, the recess 270 is dimensioned to receive the locking element 22, a compression member 24, a portion of the locking cap 26, and at least a portion of the lock nut 28. The ridged engagement between the coupling element 16 and the locking element 22 allows the first plate 12 to be coupled to the second plate 14. The second plate 214, according to one embodiment, includes a rectangular boss anti-rotation feature 272. The anti-rotation feature 272 is dimensioned to be received with a corresponding elongated recess 130 (FIG. 35) in coupling element 16. This feature limits and/or prevents the rotation of the first plate 212 and second plate 214 relative to each other about the axis of the coupling element 16 before, during, and after implantation. The second plate 214 also, according to one embodiment, includes attachment apertures 220 positioned on either side of the central aperture 268. Each aperture 220 is dimensioned to receive an extension element of an insertion tool, for example such as inserter 400 shown and described below in relation to FIGS. 52-56. The insertion tool may be used to hold and manipulate the second plate 214 as needed to properly position it on the desired spinous processes SP1, SP2.

The second plate 214 may be constructed from any of a variety to suitable materials without departing from the scope of the invention, including but not limited to titanium, polymeric materials (e.g. plastics) carbon fiber, and/or any other biologically acceptable material. The second plate 214 may also be provided having any number of suitable dimensions without departing from the scope of the invention. For example, according to one embodiment, the width of the central body 254 portion may range from 5 mm to 20 mm, the width of the end portions 256, 258 may range from 7.5 mm to 25 mm, the length of the central body portion 254 may range from 1 mm to 65 mm, the length of the end portions 256, 258 may range from 7.5 mm to 25 mm, and the thickness of the second plate 214 may range from 1.5 mm to 15 mm. It will be appreciated, however, that these dimensions are provided as examples of those that may be employed with the spinous process fixation system 210 of the present invention and any number of suitable modifications may be made depending upon a variety of factors without departing from the scope of the invention.

The remaining components and features of the spinous process fixation system 210, including the coupling element 16 and locking assembly 18 (including the locking element 22, compression cap 24, locking cap 26, and lock nut 28) are identical to those shown and described in relation to spinous process fixation system 10, rendering further discussion duplicative and unnecessary. It is to be understood that those components form a part of the example shown in FIGS. 39-43 and the above disclosure is applicable to the currently described embodiment.

FIGS. 44-51 illustrate an example of a spinous process fixation system 310 according to a third embodiment of the present invention. Spinous process fixation system 310 is substantially similar to the spinous process fixation system 10 described above, with the only difference being in the first and second plates 312, 314. Specifically, the spinous process fixation system 310 is dimensioned for a multi-level fixation (two levels, in this specific example, meaning that the spinous process fixation system 310 may be used to fix three adjacent spinous processes). All other features, including the coupling element 16 and locking assembly 18 (and component parts thereto) are identical to that described above, and thus repeat disclosure has been omitted. Furthermore, features identical to those previously discussed will be assigned the same reference numbers as set forth above.

Figure 46:
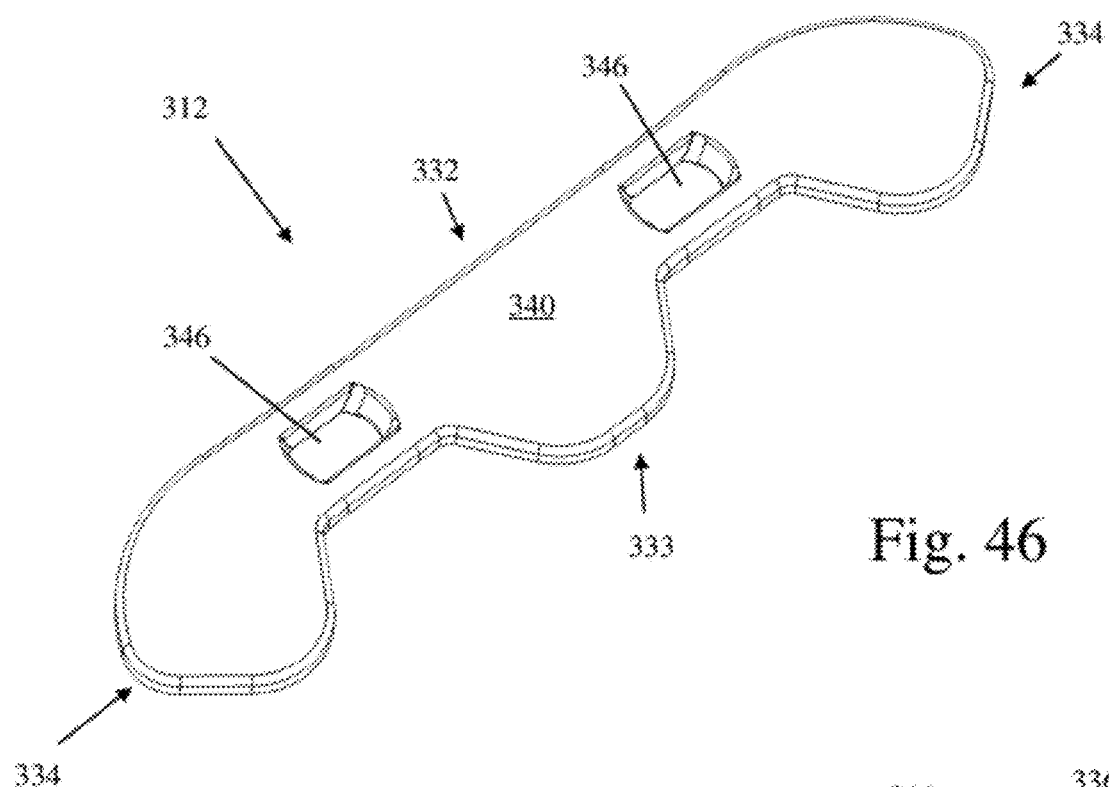
FIGS. 46-48 are top perspective, bottom perspective, and bottom plan views, respectively, of an example of a first plate forming part of the spinous process fixation system of FIG. 44.
Figure 47:
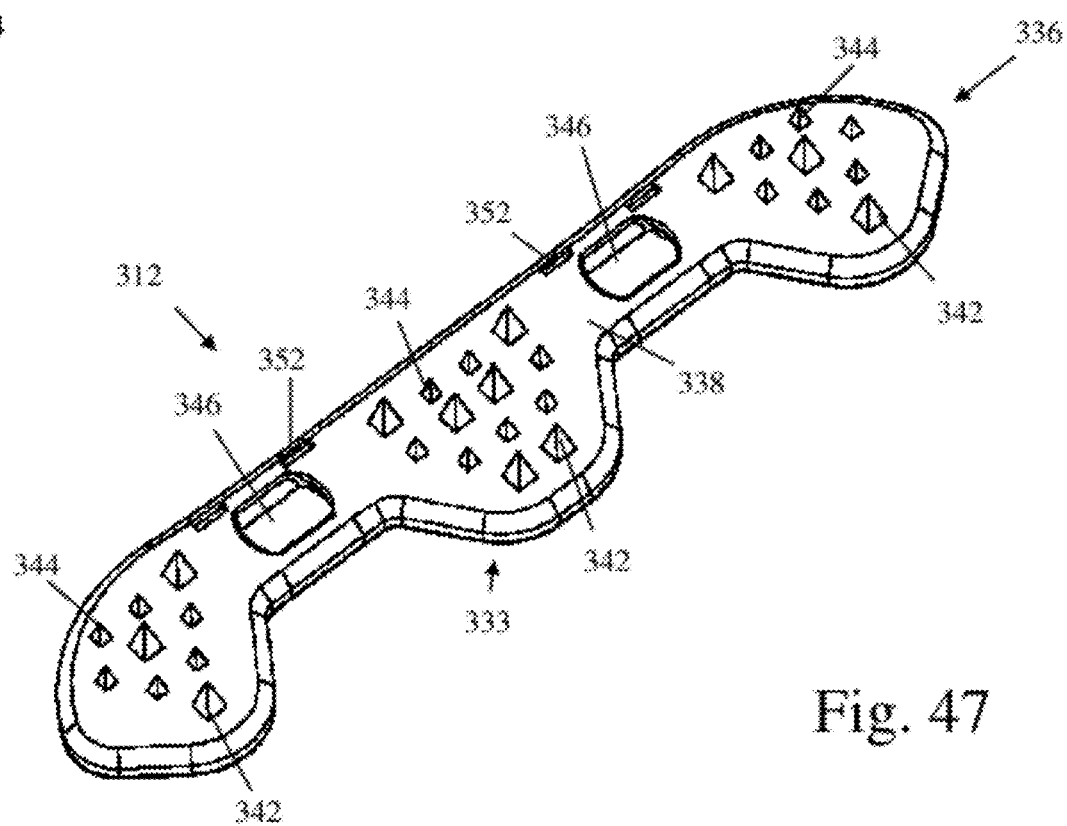
Figure 48:
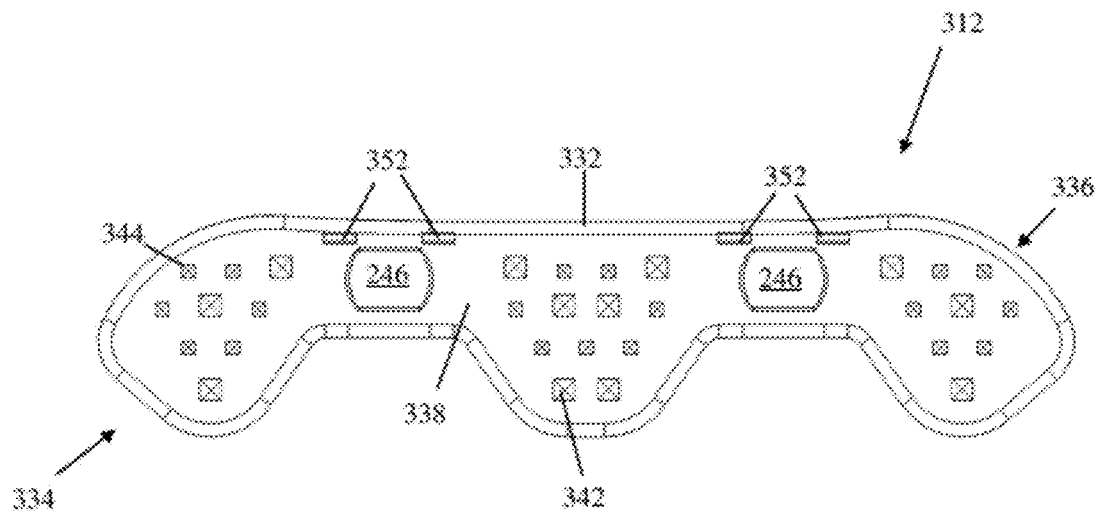

The first plate 12 will now be described with specific reference to FIGS. 46-48. The first plate 312 includes a central body portion 332 extending between a pair of end portions 334, 336. The central body portion 332 further includes a middle fixation region 333 which has a similar size, shape, and function as the end portions 334, 336. The first plate 312 further includes a first surface 338 dimensioned to face medially, or toward the second plate 314 when assembled and a second surface 340 dimensioned to face laterally, or away from the second plate 314 when assembled. The central body portion 332 may have a generally curved perimeter and has a width less than the width of the end portions 334, 336. The increased width of the middle fixation region 333 and end portions 334, 336 is designed to present a relatively large footprint on the adjacent spinous processes SP1, SP2, SP3 which helps in establishing a robust engagement therewith while avoiding protrusion beyond the spinous processes SP1, SP2, SP3. Although generally "hook" shaped in the embodiment shown, one of ordinary skill in the art will appreciate that the end portions 334, 336 (as well as the middle fixation region 333) may be provided in any number of suitable shapes including but not limited to generally rectangular, generally triangular, and generally rounded. This engagement may be augmented through the use of a plurality of major and minor spike elements 342, 344, respectively, disposed on the first surface 338 of the first plate 312, at the middle fixation region 333 and end portions 334, 336. These spike elements 342, 344 are designed to become embedded in the lateral surface of the spinous processes SP1, SP2, SP3 when the spinous process fixation system 310 is compressed in place. As described in further detail below, the spike elements 342, 344 are provided in an arrangement complimentary to that of the spike elements 364, 366 of the second plate 314 to increase purchase within the spinous process bone.

The first plate 312 includes a pair of fixation apertures 346 each dimensioned to receive a proximal end 132 of the coupling element 16. More specifically, the fixation apertures 346 are "truncated spherical" recesses having straight sides 348 and semi-spherical end regions 350. The straight sides 348 and semi-spherical end regions 350 are dimensioned to receive the generally straight sides 126 and semi-spherical end regions 128 of the head 120 of the coupling element 16 (FIGS. 35-37). The fixation apertures 346 are positioned on either side of the middle fixation region 333 such that one fixation aperture 346 is between the middle fixation region 333 and the first end portion 334 and one fixation aperture 346 is between the middle fixation region 333 and the second end portion 336. This alignment is such that the coupling elements 16 will extend through the interspinous process spaces. The first plate 312 also, according to one embodiment, includes elongated recesses 352 formed within first surface 338 and positioned on either side of the fixation apertures 346. Each recess 352 is dimensioned to receive an extension element of an insertion tool, for example such as inserter 400 shown and described below in relation to FIGS. 52-56. The insertion tool may be used to hold and manipulate the first plate 212 as needed to properly position it on the desired spinous processes SP1, SP2, SP3.

The first plate 312 may be constructed from any of a variety to suitable materials without departing from the scope of the invention, including but not limited to titanium, polymeric materials (e.g. plastics such as poly-ether-ether-ketone) carbon fiber, and/or any other biologically acceptable material. The first plate 312 may also be provided with any number of suitable dimensions without departing from the scope of the invention. For example, according to one embodiment, the width of the central body portion 332 may range from 5 mm to 20 mm, the width of the end portions 334, 336 may range from 7.5 mm to 25 mm, the length of the central body portion 332 may range from 1 mm to 65 mm, the length of the end portions 334, 336 may range from 7.5 mm to 25 mm, and the thickness of the first plate 312 may range from 1.5 mm to 15 mm. It will be appreciated, however, that these dimensions are provided as examples of those that may be employed with the spinous process fixation system 310 of the present invention and any number of suitable modifications may be made depending upon a variety of factors without departing from the scope of the invention.

Figure 49:
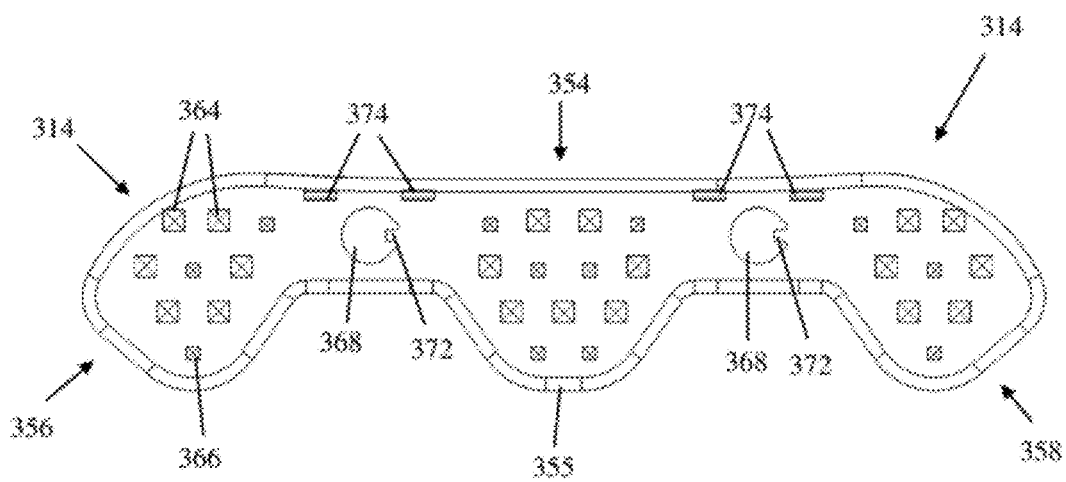
FIGS. 49-51 are bottom plan, top perspective, and bottom perspective views, respectively, of an example of a second plate forming part of the spinous process fixation system of FIG. 44.
Figure 50:
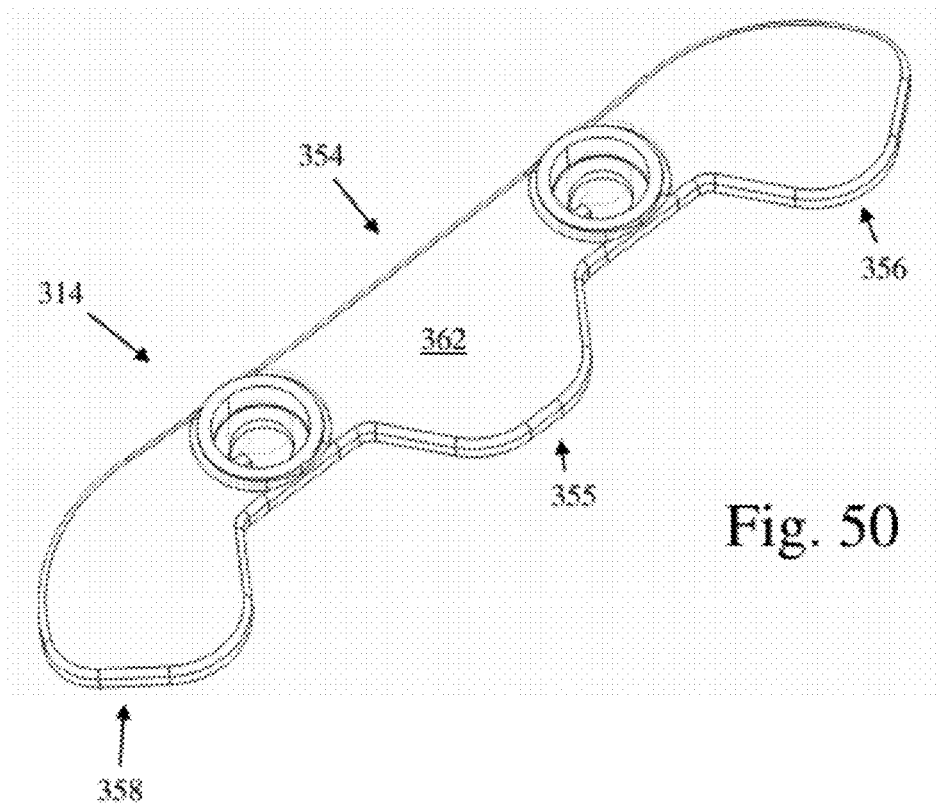
Figure 51:
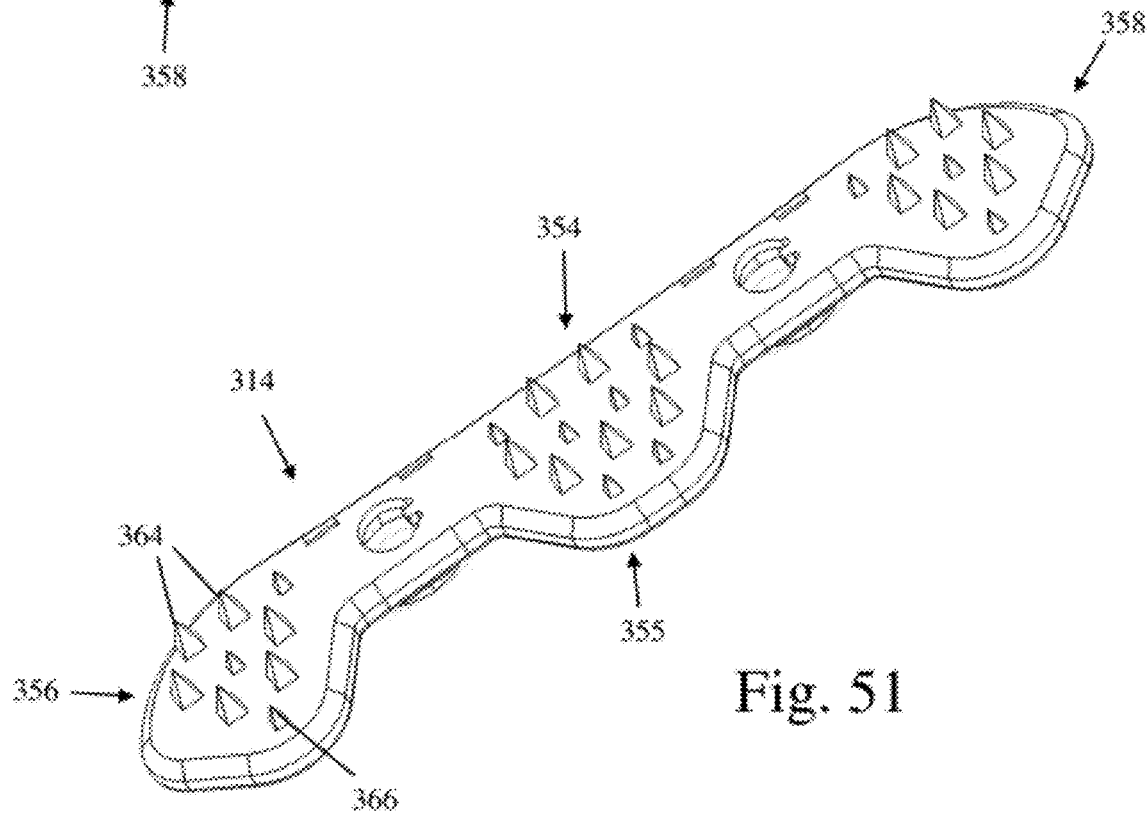
Figure 52:
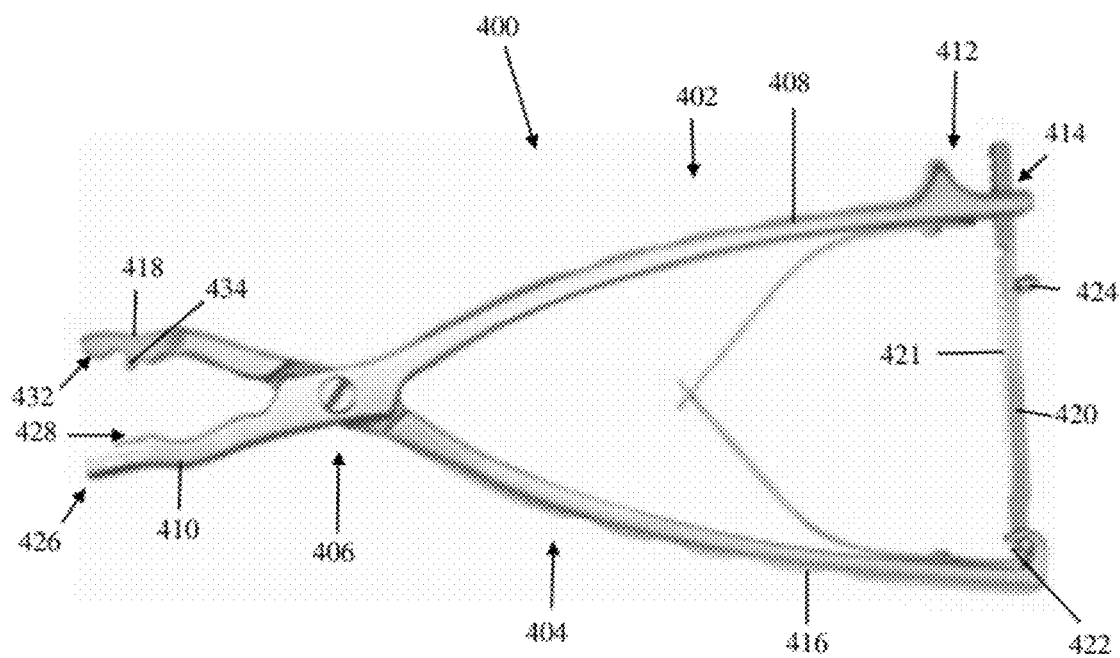
FIG. 52 is a plan view of one example of an insertion device configured for use with the spinous process fixation system of FIG. 4.

Referring to FIGS. 49-51, the second plate 314 includes similar general features as the first plate 312. The second plate 314 includes a central body portion 354 extending between end portions 356, 358. The central body portion 354 further includes a middle fixation region 355 which has a similar size, shape, and function as the end portions 356, 358. The second plate 314 further includes a first surface 360 dimensioned to face medially, or toward the first plate 312 when assembled and a second surface 362 dimensioned to face laterally, or away from the first plate 312 when assembled. The central body portion 354 has a generally curved perimeter and has a width less than the width of the end portions 356, 358. The increased width of the middle fixation region 355 and end portions 356, 358 is designed to present a relatively large footprint on the adjacent spinous processes SP1, SP2, SP3 which helps in establishing a robust engagement therewith while avoiding protrusion beyond the spinous processes SP1, SP2, SP3. Although generally "hook" shaped in the embodiment shown, one of ordinary skill in the art will appreciate that the end portions 356, 358 (and middle fixation region 355) may be provided in any number of suitable shapes including but not limited to generally rectangular, generally triangular, and generally rounded. This engagement may be augmented through the use of a plurality of major and minor spike elements 364, 366 disposed on the medial facing surface of the middle fixation region 355 and end portions 356, 358. These spike elements 364, 366 are designed to become embedded in the lateral surface of the spinous processes SP1, SP2 when the spinous process fixation system 310 is compressed in place. The spike elements 364, 366 are provided in an arrangement complimentary to that of the spike elements 342, 344 of the first plate 312 to increase purchase within the spinous process bone. For example, when the first and second plates 312, 314 are attached to the bone, major spike elements 342 on first plate 312 will be aligned with minor spike elements 366 on second plate 314, and major spike elements 364 on second plate 314 will be aligned with minor spike elements 344 on first plate 312 so as to minimize the potential for opposing spike elements to contact one another when fully inserted. If this were to happen, the overall purchase of the spike elements within the bone may be reduced, leading to an unstable construct. Providing complementary opposing major and minor spike elements as shown and described herein by example minimizes this risk of "meeting in the middle" of the spinous process bone by ensuring spike elements of differing sizes are inserted into the bone opposite one another. This leads to a more stable construct.

The second plate 314 includes a pair of fixation apertures 368 dimensioned to receive a distal end 132 of the coupling element 16. More specifically, the fixation apertures 368 are each included within recesses 370 formed within the second surface 362 of the second plate 314. The recesses 370 are positioned between the middle fixation region 355 and each of the first and second end portions 356, 358 and are dimensioned to receive the assembled locking assembly 18. More specifically, as described above, the recesses 370 are dimensioned to receive the locking element 22, a compression member 24, a portion of the locking cap 26, and at least a portion of the lock nut 28. The ridged engagement between the coupling element 16 and the locking element 22 allows the first plate 312 to be coupled to the second plate 314. The second plate 314, according to one embodiment, includes a rectangular boss anti-rotation feature 372. The anti-rotation feature 372 is dimensioned to be received with a corresponding elongated recess 130 (FIG. 35) in coupling element 16. This feature limits and/or prevents the rotation of the first plate 312 and second plate 314 relative to each other about the axis of the coupling element 16 before, during, and after implantation. The second plate 314 further includes two pair of elongated recesses 374 formed within the first surface 360 and positioned on either side of the fixation apertures 368. Each elongated recess 374 is dimensioned to receive an extension element of an insertion tool, for example such as inserter 400 shown and described below in relation to FIGS. 52-56. The insertion tool may be used to hold and manipulate the second plate 314 as needed to properly position it on the desired spinous processes SP1, SP2, SP3.

The second plate 314 may be constructed from any of a variety to suitable materials without departing from the scope of the invention, including but not limited to titanium, polymeric materials (e.g. plastics) carbon fiber, and/or any other biologically acceptable material. The second plate 314 may also be provided having any number of suitable dimensions without departing from the scope of the invention. For example, according to one embodiment, the width of the central body 354 portion may range from 5 mm to 20 mm, the width of the end portions 356, 358 may range from 7.5 mm to 25 mm, the length of the central body portion 354 may range from 1 mm to 65 mm, the length of the end portions 356, 358 may range from 7.5 mm to 25 mm, and the thickness of the second plate 314 may range from 1.5 mm to 15 mm. It will be appreciated, however, that these dimensions are provided as examples of those that may be employed with the spinous process fixation system 310 of the present invention and any number of suitable modifications may be made depending upon a variety of factors without departing from the scope of the invention.

The remaining components and features of the spinous process fixation system 310, including the coupling element 16 and locking assembly 18 (including the locking element 22, compression cap 24, locking cap 26, and lock nut 28) are identical to those shown and described in relation to spinous process fixation system 10, rendering further discussion duplicative and unnecessary. It is to be understood that those components form a part of the example shown in FIGS. 44-51 and the above disclosure is applicable to the currently described embodiment.

FIGS. 52-56 illustrate one example of an insertion tool 400 for use with any of the spinous process fixation systems 10, 210, 310 described above. The insertion tool 400 includes first and second elongated members 402, 404 pivotably coupled together about a pivot point 406. The first elongated member 402 includes a proximal handle 408 and a distal implant engagement region 410. The proximal handle 408 has a proximal end 412 including a bifurcation 414 for receiving a ratchet arm 420 including a plurality of teeth 421. The second elongated member 404 includes a proximal handle 416 and a distal implant engagement region 418. The insertion tool 400 further includes a ratchet arm 420 hingedly connected with the handle 416 of the second elongated member 404 at a proximal hinge point 422. The ratchet arm further includes a lock stop 424 for preventing over compression of the spinous process fixation system 10 prior to implantation into the affected surgical target site.

Figure 53:
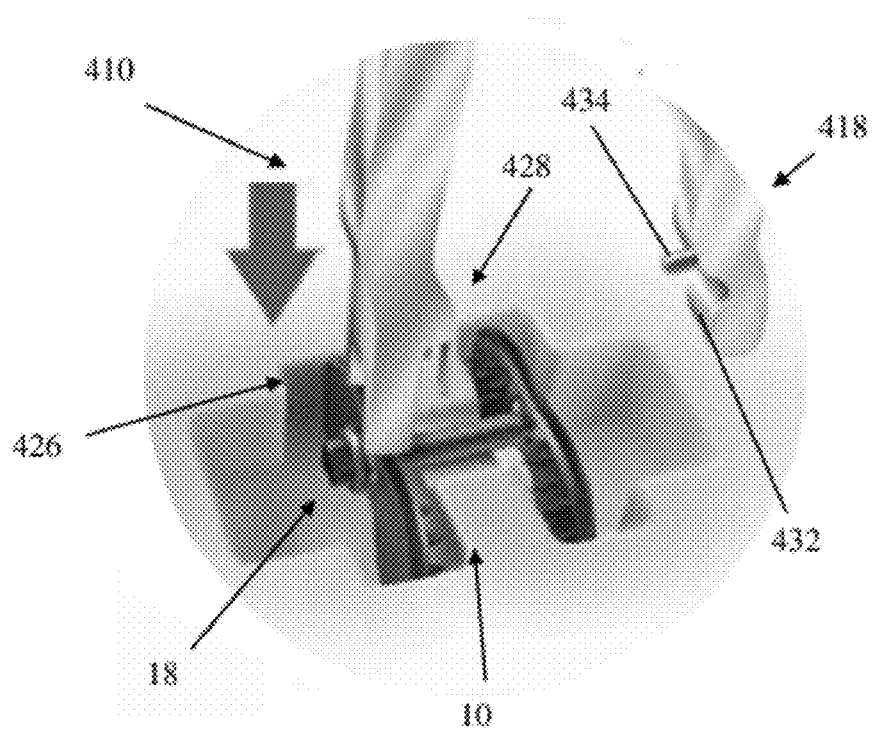
FIGS. 53-55 are perspective views of steps in a process of engaging the insertion device of FIG. 52 with the spinous process fixation system of FIG. 4.
Figure 54:
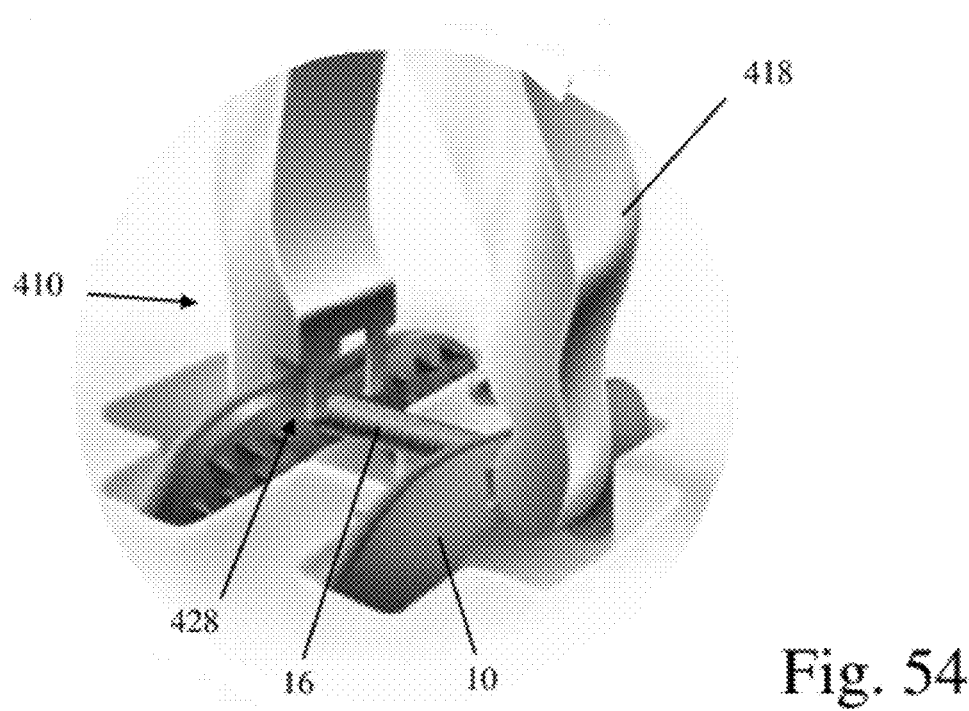

The distal implant engagement region 410 of the first elongated member 402 includes a first pronged region 426 and a second pronged region 428. The first pronged region 426 is dimensioned to engage the second surface 62 of the second plate 14 while avoiding the locking assembly 18, as shown in FIG. 53. The second pronged region 428 is dimensioned to engage the first surface 60 of the second plate 12 while avoiding the coupling element 16, as shown in FIG. 54. More specifically, the second pronged region 428 includes a plurality of tanged tips 430 dimensioned to be received within the elongated recesses 74 of the second plate 14, enabling the inserter 400 to grab the second plate 14.

The distal implant engagement region 418 of the second elongated member 404 includes a generally rounded engagement feature 432 configured to engage the first plate 12. More specifically, the engagement feature 432 is dimensioned to seat at least partially in the aperture 46 of the first plate 12. The distal implant engagement region 418 further includes a post 434 extending generally perpendicularly from the engagement region 418.

Figure 55:
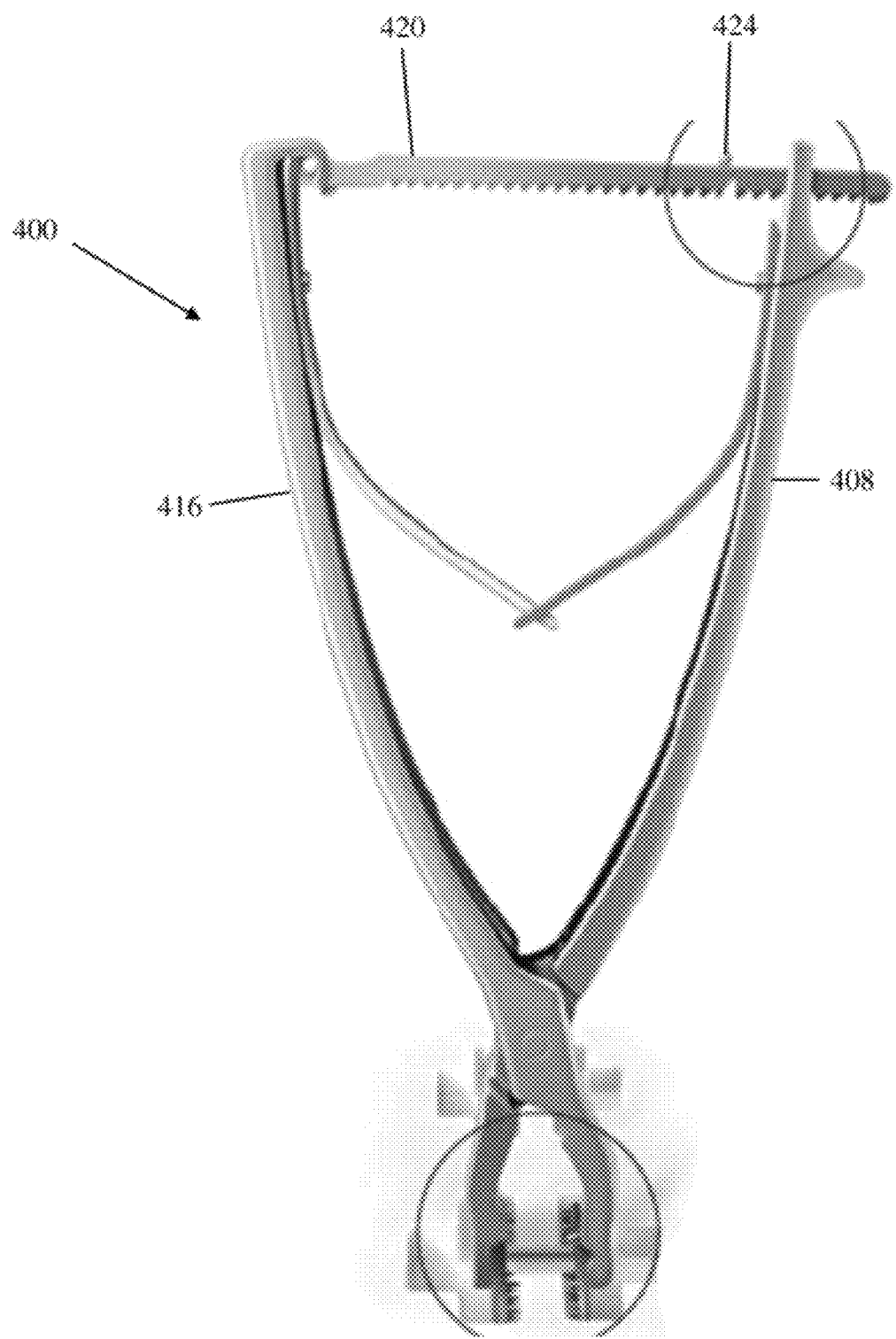
Figure 56:
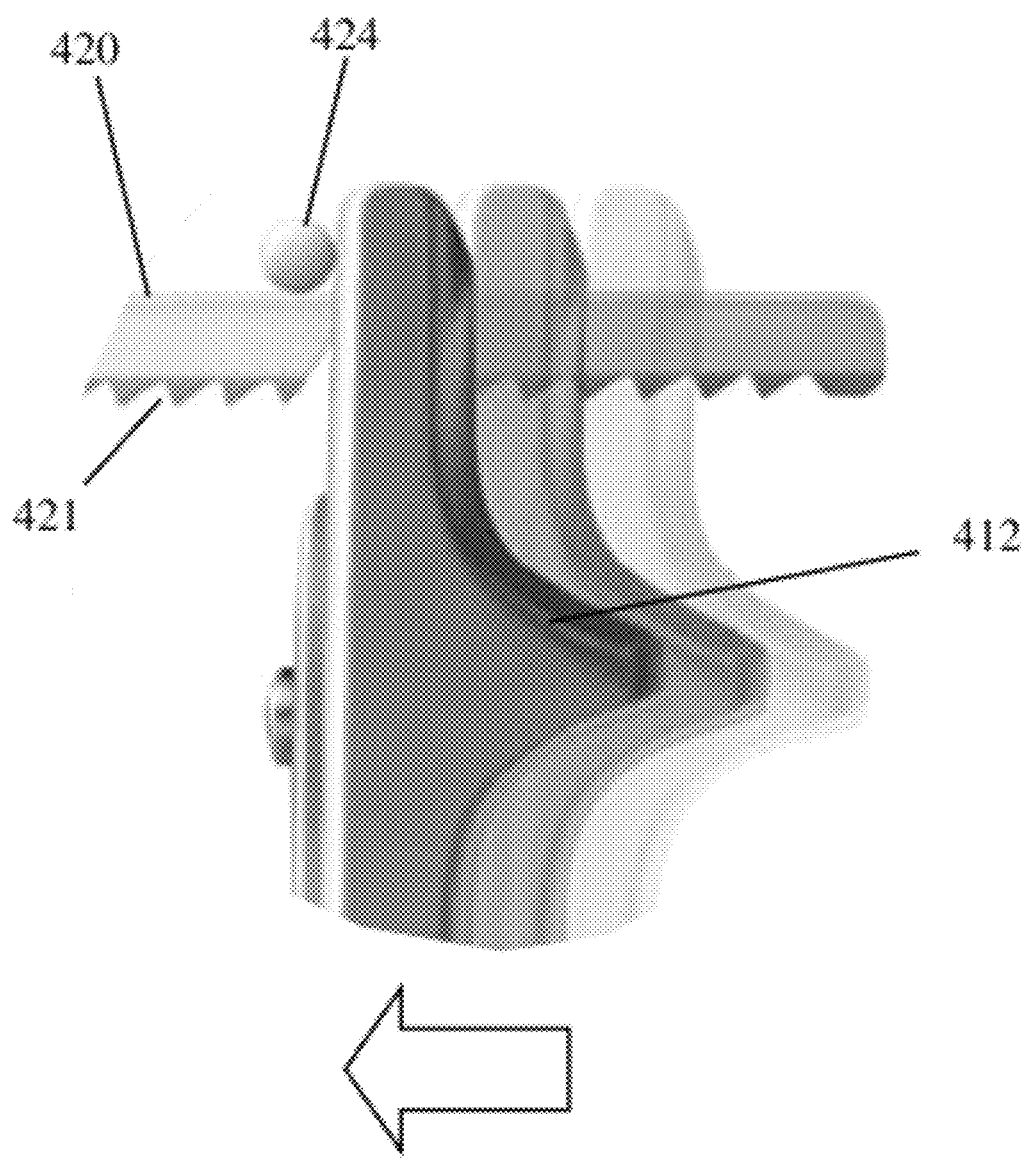
FIG. 56 is a perspective view of a portion of the proximal end of the insertion device of FIG. 52.

FIGS. 53-55 illustrate the steps involved in using the inserter 400 to controllably capture the spinous process fixation system 10 in advance of implanting it into a surgical target site. First, as shown in FIG. 53, the distal implant engagement region 410 of the first elongated member 402 is positioned such that it engages the second plate 14. Next, as shown in FIG. 54, the distal implant engagement region 418 of the second elongated member 404 is positioned such that it engages the first plate 12. As shown in FIG. 55, when the inserter is properly positioned relative to the spinous process fixation system 10, the handles 408, 418 are squeezed together to create a compressive force on the spinous process fixation system 10. The ratchet arm 420 functions to maintain the compressive force on the spinous process fixation system 10 through implantation so that it does not dislodge from the inserter 400. To prevent over compression of the spinous process fixation system 10 prior to insertion (and prevent the need for the surgeon to spend valuable time unlocking the system to allow for insertion), the ratchet arm 420 is provided with a lock stop 424. As illustrated in FIG. 56, the lock stop 424 will halt advancement of the handle 408 past a certain point to prevent this over compression. Once the spinous process fixation system 10 is favorably seated relative to the surgical target site, the ratchet arm 420 can be pivoted away from the handle 408 so that the lock stop 424 is no longer engaged. This will allow the user to squeeze the handle further to employ enough force to fully seat the spinous process fixation system 10 onto the spinous processes. Once this has happened, the operative corridor may be closed and the procedure is concluded.

The embodiments described herein are intended to rigidly fix two spinous processes relative to one another. The spinous process fixation system 10 may be implanted via a traditional "open" procedure or a minimally invasive procedure. In a minimally invasive procedure, the spinous process fixation system 10 may be implanted generally posteriorly through a single incision (e.g. where the first plate 12 and second plate 14 are passed through the same incision) or multiple incisions (e.g. where the first plate 12 is passed through one incision and the second plate 14 is passed through a second incision). During a uni-portal introduction, the surgeon may pass both the first plate 12 and the second plate 14 into position on either side of adjacent spinous processes SP1, SP2 at the same time. During a bi-portal introduction, the surgeon may first insert the first plate 12 to engage one side of the spinous processes SP1, SP2 and then insert the second plate 14 against the other side of spinous processes SP1, SP2. In either event, the surgeon can adjust the position of the end portions of the first plate 12 and second plate 14 so that the spike members are engaged into the spinous processes SP1, SP2. At this point, compression instrumentation may be applied to press the plates toward each other, whereupon the spikes enter the spinal processes SP1, SP2. Following the full seating of the plates on the spinal processes SP1, SP2, the coupling element 16 is tightened using any number of suitable instruments. When the surgeon is satisfied with the degree to which the first plate 12 and second plate 14 are locked together, then the site may be closed up, completing the stabilization procedure.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A plating system for stabilizing a first spinous process and a second spinous process, each of said spinous processes having a first side and a second side, said plating system comprising:

a first plate including a first surface for contacting said first sides of said first and second spinous processes, a second surface opposite said first surface, a first end portion, a second end portion, and a generally elongated body portion extending between said first and second end portions, wherein said elongated body portion contains a first central aperture and a recess therein;

a locking element positioned within said recess of the first central aperture, wherein said locking element comprises a generally circular canted spring coil member having outer and inner circumferences and an aperture bounded by the inner circumference, said aperture dimensioned to receive said elongated connector;

a second plate including a first surface for contacting second sides of said first and second spinous processes, a second surface opposite said first surface, a first end portion, a second end portion, and a generally elongated body portion having a second central aperture extending between said first and second end portions; and an elongated connector element extending through said first and second central apertures, said connector element reversibly coupled to at least one of said first and second plates, wherein said elongated connector element includes a plurality of non-threaded ridges and an elongated recess extending substantially the length of said connector element.

2. The plating system of claim 1, wherein said first surface of said first plate includes a first contact region dimensioned to engage at least a portion of said first side of said first spinous process and a second contact region dimensioned to engage at least a portion of said first side of said second spinous process, and said first surface of said second plate includes a first contact region dimensioned to engage at least a portion of said second side of said first spinous process and a second contact region dimensioned to engage at least a portion of said second side of said second spinous process.

3. The plating system of claim 2, wherein said first contact region of said first plate is located on said first end portion of said first plate, said second contact region of said first plate is located on said second end portion of said first plate, said first contact region of said second plate is located on said first end portion of said second plate, and said second contact region of said second plate is located on said second end portion of said second plate.

4. The plating system of claim 3, wherein said first and second contact regions of said first and second plates each include a plurality of anti-migration features to secure the first and second plates to said first and second spinous processes.

5. The plating system of claim 4, wherein said anti-migration features comprise spike elements.

6. The plating system of claim 5, wherein said spike elements include a plurality of major and minor spike elements.

7. The plating system of claim 6, wherein said major spike elements of the first plate are aligned with said minor spike elements of the second plate, and said minor spike element of the first plate are aligned with said major spike elements of the second plate.

8. The plating system of claim 1, wherein at least one of said first and second end portions of said first and second plates is at least one of generally rectangular, generally triangular, and generally rounded.

9. The plating system of claim 1, wherein said connector element includes a shaped head element and a shaft element.

10. The plating system of claim 1, wherein said first central aperture of the first plate further includes an anti-rotation element dimensioned to engage said elongated recess to prevent rotation of said connector element.

11. The plating system of claim 1, wherein at least one of said first and second end portions of said first and second plates has a width dimension within a range from 7.5 millimeters to 25 millimeters.

12. The plating system of claim 1, wherein said elongated body portions of said first and second plates have a width dimension within a range from 5 millimeters to 20 millimeters.

13. The plating system of claim 1, wherein at least one holding element temporarily and immovably attaches the said connector element to the second plate.

14. The plating system of claim 13, wherein said holding element includes a spot weld.

15. The plating system of claim 1, further comprising a compression member to facilitate uni-directional movement of the connector element through said central aperture of the first plate.

* * * * *